US009434765B2

(12) United States Patent
Rodríguez Medina

(10) Patent No.: US 9,434,765 B2
(45) Date of Patent: Sep. 6, 2016

(54) HIGH AFFINITY SUMO TRAPS

(75) Inventor: Manuel Salvador Rodríguez Medina, Vizcaya (ES)

(73) Assignee: ASOCIACIÓN CENTRO DE INVESTIGACIÓN COOPERATIVA EN BIOCIENCIAS-CIC BIOGUNE, Vizcaya (ES)

( * ) Notice: Subject to any disclaimer, the term of this patent is extended or adjusted under 35 U.S.C. 154(b) by 0 days.

(21) Appl. No.: 14/119,343

(22) PCT Filed: Mar. 8, 2012

(86) PCT No.: PCT/EP2012/054039
§ 371 (c)(1),
(2), (4) Date: Feb. 19, 2014

(87) PCT Pub. No.: WO2012/159782
PCT Pub. Date: Nov. 29, 2012

(65) Prior Publication Data
US 2014/0165222 A1    Jun. 12, 2014

Related U.S. Application Data

(60) Provisional application No. 61/489,490, filed on May 24, 2011.

(51) Int. Cl.
C07K 7/08        (2006.01)
C07K 14/47       (2006.01)
G01N 33/566      (2006.01)
C12N 9/00        (2006.01)

(52) U.S. Cl.
CPC ............. *C07K 7/08* (2013.01); *C07K 14/47* (2013.01); *C12N 9/93* (2013.01); *C12Y 603/02019* (2013.01); *G01N 33/566* (2013.01)

(58) Field of Classification Search
None
See application file for complete search history.

(56) References Cited

U.S. PATENT DOCUMENTS 8,716,441 B2 * 5/2014 Rodriguez Medina et al. ............... 530/350

OTHER PUBLICATIONS

Hecker, et al. (2006) "Specification of SUMO1- and SUMO2-interacting Motifs", The Journal of Biological Chemistry vol. 281, No. 23, pp. 16117-16127.*
Altschul SF, et al., 1990. Basic local alignment search tool. J Mol Biol. 215(3):403-10.
Bernier-Villamor V., et al., 2002.Structural basis for E2-mediated SUMO conjugation revealed by a complex between ubiquitin conjugating enzyme Ubc9 and RanGAP1. Cell 108, 345-356.
Bruderer R, et al., 2011. Purification and identification of endogenous polySUMO conjugates. EMBO Rep. Feb.;12(2):142-8.
Geiss-Friedlander R., et al., 2007. Concepts in SUMOylation: a decade on. Nature reviews molecular cell biology 8;947-956.
Golebiowski F., et al., 2009. System-Wide Changes to SUMO Modifications in Response to Heat Shock. Sci. Signal., 2(72) 24.
Hecker C. M., et al., 2006. Specification of SUMO1- and SUMO2-interacting motifs. J. Biol. Chem. 281, 16117-16127.
Hay R. 2005. SUMO: A History of Modification. Molecular Cell, 18, 1-12.
Hayashi T., et al., 2002. Ubc9 is essential for viability of higher eukaryotic cells. Exp. Cell Res. 280, 212-221.
Johnson E. S. 2004. Protein modification by SUMO. Annu. Rev. Biochem 73:355-382.
Kagey M.H., et al., 2003. The polycomb protein Pc2 is a SUMO E3. Cell 113, 127-137.
Kahyo T., et al., 2001. Involvement of PIAS1 in the sumoylation of tumor suppressor p53. Mol. Cell 8 (3): 713-8.
Kerscher O., et al., 2006. Modification of proteins by ubiquitin and ubiquitin-like proteins. Annu. Rev. Cell Dev. Biol. 22, 159-180.
Lapenta, V., et al., 1997. SMT3A, a human homologue of the *S. cerevisiae* SMT3 gene, maps to chromosome 21qter and defines a novel gene family. Genomics 40, 362-366.
Matunis, M. J., et al., 1996. A novel ubiquitin-like modification modulates the partitioning of the Ran-GTPase-activating protein RanGAP1 between the cytosol and the nuclear pore complex. J. Cell Biol. 135,1457-1470.
Mahajan, R., et al., (1997) A small ubiquitin-related polypeptide involved in targeting RanGAP1 to nuclear pore complex protein RanBP2. Cell 88, 97-107.
Miteva M., et al., Sumoylation as a Signal for Polyubiquitylation and Proteasomal Degradation. 2010. Chapter 16. pp. 195-214. Bookshelf ID: NBK25447 Conjugation and Deconjugation of Ubiquitin Family Modifiers, edited by Marcus Groettrup.
Rodriguez MS, et al., SUMO-1 modification activates the transcriptional response of p53. 1999. EMBO J. Nov. 15;18(22):6455-61.
Rodriguez M. S., et al., 2001. SUMO-1 conjugation in vivo requires both a consensus modification motif and nuclear targeting. J. Biol. Chem. 276, 12654-12659.
Sambrook J., et al., Molecular cloning, a Laboratory Manual. 1989. 2nd ed., Cold Spring Harbor Laboratory Press, N.Y., vol. 1-3.
Saitoh H, Hinchey J. 2000. Functional heterogeneity of small ubiquitin-related protein modifiers SUMO-1 versus SUMO-2/3. J Biol Chem;275:6252-6258.

(Continued)

*Primary Examiner* — Robert M Kelly
(74) *Attorney, Agent, or Firm* — Tristan A. Fuierer; Moore & Van Allen, PLLC

(57) ABSTRACT

The potential use of these "SUMO receptors" to isolate SUMOylated targets has been considered using the SIM sequences of the SUMO-dependent ubiquitin-protein ligase RNF4. RFN4 contains 4 SIM sequences known to interact with SUMOylated proteins. The capacity of the SIM2 and SIM3 of RNF4 to purify SUMOylated proteins was increased when in the present invention it was disposed in tandem up to 4 SIM sequences. In a preferred embodiment to increase flexibility and functionality of this SUMO-trap, we have changed the natural linkers resulting in a broader capture of SUMOylated proteins. This Tandem SUMO Interacting Motifs (TSIMs) or SUMO-Binding Entities (SUBEs) system disclosed in the present invention is useful to capture polySUMOylated proteins from cell extracts. Therefore, in another embodiment of the present invention, TSIMs or SUBEs can be used for the identification SUMO substrates and the study of SUMO-regulated processes.

18 Claims, 14 Drawing Sheets

(56) References Cited

OTHER PUBLICATIONS

Sampson DA, et al., 2001. The small ubiquitin-like modifier-1(SUMO-1) consensus sequence mediates Ubc9 binding and is essential for SUMO-1 modification. J Biol Chem. 276(24):21664-9.

Seufert, W., et al., 1995. Role of ubiquitin-conjugating enzyme in degradation of S- and M-phase cyclins. Nature 373, 78-81.

Seeler, J., et al., 2003. Nuclear and unclear functions of SUMO. Nat Rev Mol Cell Biol. 9:690-9.

Schmidt, D., et al., 2002. Members of the PIAS family act as SUMO ligases for c-Jun and p53 and repress p53 activity. Proc. Natl. Acad. Sci. U.S.A. 99, 2872-2877.

Song, J., et al., 2004. Identification of a SUMO-binding motif that recognizes SUMO-modified proteins. Proc. Natl Acad. Sci. USA 101, 14373-14378.

Tatham M.H., et al., 2001. Polymeric chains of SUMO-2 and SUMO-3 are conjugated to protein substrates by SAE1/SAE2 and Ubc9. J. Biol. Chem. 276, 35368-35374.

Tatham, M,.H., et al., 2008. RNF4 is a poly-SUMO-specific E3 ubiquitin ligase required for arsenic-induced PML degradation. Nat Cell Biol.10(5):538-46.

Yeh, E. T. 2009. SUMOylation and De-SUMOylation: wrestling with life's processes. J. Biol. Chem. 284, 8223-8227.

Wilkinson K., et al., 2010. Mechanisms, regulation and consequences of protein SUMOylation. Biochem. J. 428, 133-145.

Xu J., et al., A novel method for high accuracy sumoylation site prediction from protein sequences. BMC Bioinformatics 9,8.

International Search Report, May 7, 2012.

\* cited by examiner

TSIM 1 (RNF4)

```
     G   S   E   T   A   G   D   E   I   V   D   L   G   G   G   G   S   G   G   G   G   S   G   G   G   G   I   V   D   L   G   G   G   G   S   G   G   G   G   S   G   G   G   G   I   V   D   L   G   G   G   G   S   G   G   G   G   S   G   G   G   G   I   V   D   L
5'- GGA TCT GAA ACT GCT GGA GAT GAA ATT GTG GAC CTC GGT GGG GGA GGC GGT GGG GGA GGC GGT GGG GGA ATT GTG GAC CTC GGT GGG GGA GGC GGT GGG GGA GGC GGT GGG GGA ATT GTG GAC CTC GGT GGG GGA GGC GGT GGG GGA GGC GGT GGG GGA ATT GTG GAC CTC
     T   C   E   S   L   E   P   V   V   V   D   L
ACT TGT GAA TCT TTA GAG CCT GTG GTG GTT GAT CTG
     T   C   E   S   L   E   P   V   V   V   D   L
ACT TGT GAA TCT TTA GAG CCT GTG GTG GTT GAT CTG
     T   C   E   S   L   E   P   V   V   V   D   L
ACT TGT GAA TCT TTA GAG CCT GTG GTG GTT GAT CTG G -3'
```

TSIM 2 (RNF4 synthetic)

```
     G   S   G   G   G   G   S   G   G   G   G   S   G   G   G   G   I   V   D   L   G   G   G   G   S   G   G   G   G   S   G   G   G   G   I   V   D   L   G   G   G   G   S   G   G   G   G   S   G   G   G   G   I   V   D   L   G   G   G   G   S   G   G   G   G   S   G   G   G   G   I   V   D   L
5'- GGA TCT GGC GGT GGA GGA AGC GGT GGA GGA GGC GGT GGA GGG GGT GGG ATT GTG GAC CTC GGT GGA GGC GGT GGA GGA GGC GGT GGA GGG GGT GGG ATT GTG GAC CTC GGT GGA GGC GGT GGA GGA GGC GGT GGA GGG GGT GGG ATT GTG GAC CTC
     G   S   G   G   G   G   S   G   G   G   G   S   G   G   G   G   V   V   D   L
GGA TCT GGC GGT GGA GGA GGC GGT GGA GGA GGC GGT GGA GGG GGT GTC GTG GTT GAT CTG
     G   V   V   D   L
GGT GGA GGC GGT GGA GGA GGC GGT GGA GGG GGT GTC GTG GTT GAT CTG
     G   V   V   D   L
GGT GGA GGC GGT GGA GGA GGC GGT GGA GGG GGT GTC GTG GTT GAT CTG G -3'
```

FIGURE 4

I- Cloning, Transformation and Productions of TSIMs
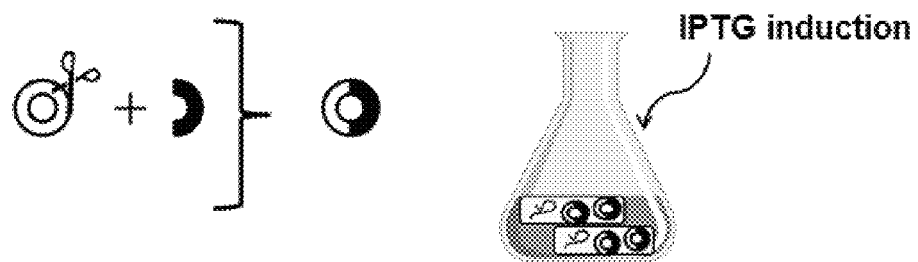
II-TSIMs Purification
Bacterial lysis by sonication and centrifugation
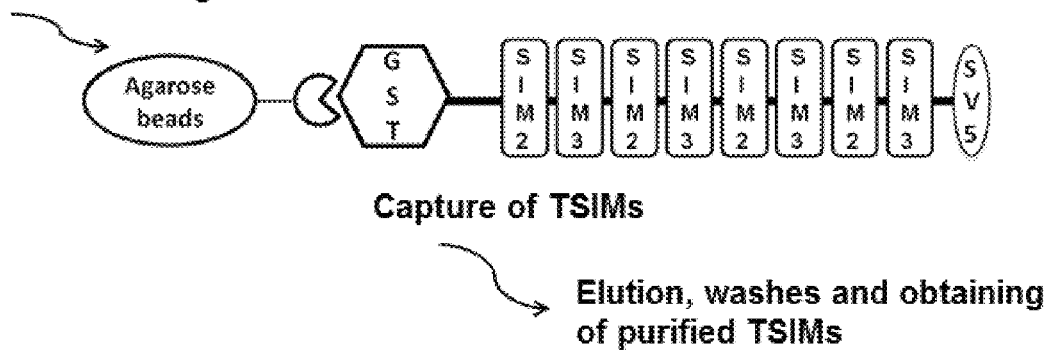
Capture of TSIMs
Elution, washes and obtaining of purified TSIMs
FIGURE 5

SURFACE PLASMON RESONANCE
B
SUBE 1
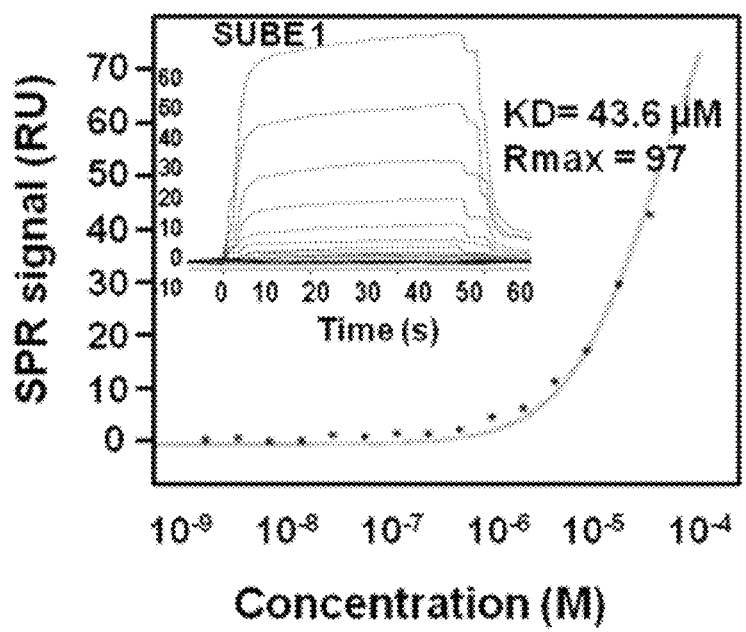
SUBE 2
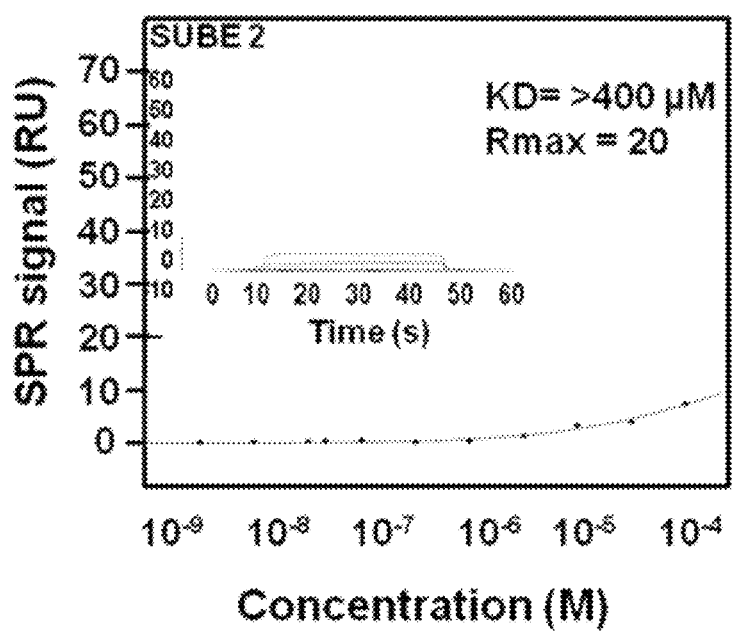
FIGURE 9 (cont.)

SEQUENCE LISTING

```
<160> NUMBER OF SEQ ID NOS: 13

<210> SEQ ID NO 1
<211> LENGTH: 72
<212> TYPE: DNA
<213> ORGANISM: Artificial Sequence
<220> FEATURE:
<223> OTHER INFORMATION: Synthetic Construct

<400> SEQUENCE: 1
gatcttaaac tgctggagat gaaattgtgg acctcacttg tgaatcttta gagcctgtgg      60
tggttgatct gg                                                          72

<210> SEQ ID NO 2
<211> LENGTH: 75
<212> TYPE: DNA
<213> ORGANISM: Artificial Sequence
<220> FEATURE:
<223> OTHER INFORMATION: Synthetic Construct

<400> SEQUENCE: 2
gatcccagat caaccaccac aggctctaaa gattcacaag tgaggtccac aatttcatca      60
tctccagcag tttca                                                       75

<210> SEQ ID NO 3
<211> LENGTH: 72
<212> TYPE: DNA
<213> ORGANISM: Artificial Sequence
<220> FEATURE:
<223> OTHER INFORMATION: Synthetic Construct

<400> SEQUENCE: 3
gatctggcgg tggaggaggc ggtgggattg tggacctcgg tggaggcgga gggggtggcg      60
tggttgatct gg                                                          72

<210> SEQ ID NO 4
<211> LENGTH: 72
<212> TYPE: DNA
<213> ORGANISM: Artificial Sequence
<220> FEATURE:
<223> OTHER INFORMATION: Synthetic Construct

<400> SEQUENCE: 4
gatcccagat caaccacgcc acccctccg cctccaccga ggtccacaat cccaccgcct       60
cctccaccgc ca                                                          72

<210> SEQ ID NO 5
<211> LENGTH: 5058
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (258)..(918)
<223> OTHER INFORMATION: Glutathione S-transferase (GST)
<220> FEATURE:
<221> NAME/KEY: misc_feature
<222> LOCATION: (951)..(968)
<223> OTHER INFORMATION: His6 tail
<220> FEATURE:
<221> NAME/KEY: exon
<222> LOCATION: (1002)..(1043)
<223> OTHER INFORMATION: Sv5 epitope
<220> FEATURE:
<221> NAME/KEY: misc_feature
<222> LOCATION: (1456)..(2314)
<223> OTHER INFORMATION: Ampiciline resistance
<220> FEATURE:
<221> NAME/KEY: misc_feature
<222> LOCATION: (3407)..(4487)
<223> OTHER INFORMATION: lacI<

<400> SEQUENCE: 5
```

| | |
|---|---|
| acgttatcga ctgcacggtg caccaatgct tctggcgtca ggcagccatc ggaagctgtg | 60 |
| gtatggctgt gcaggtcgta atcactgca taattcgtgt cgctcaaggc gcactcccgt | 120 |
| tctggataat gttttttgcg ccgacatcat aacggttctg gcaaatattc tgaaatgagc | 180 |
| tgttgacaat taatcatcgg ctcgtataat gtgtggaatt gtgagcggat aacaatttca | 240 |
| cacaggaaac agtattcatg tcccctatac taggttattg gaaaattaag ggccttgtgc | 300 |
| aacccactcg acttcttttg gaatatcttg aagaaaaata tgaagagcat ttgtatgagc | 360 |
| gcgatgaagg tgataaatgg cgaaacaaaa agtttgaatt gggtttggag tttcccaatc | 420 |
| ttccttatta tattgatggt gatgttaaat taacacagtc tatggccatc atacgttata | 480 |
| tagctgacaa gcacaacatg ttgggtggtt gtccaaaaga gcgtgcagag atttcaatgc | 540 |
| ttgaaggagc ggtttttggat attagatacg gtgtttcgag aattgcatat agtaaagact | 600 |
| ttgaaactct caaagttgat tttcttagca agctacctga atgctgaaa atgttcgaag | 660 |
| atcgtttatg tcataaaaca tatttaaatg gtgatcatgt aacccatcct gacttcatgt | 720 |
| tgtatgacgc tcttgatgtt gttttataca tggacccaat gtgcctggat gcgttcccaa | 780 |
| aattagtttg ttttaaaaaa cgtattgaag ctatcccaca aattgataag tacttgaaat | 840 |
| ccagcaagta tatagcatgg cctttgcagg gctggcaagc cacgtttggt ggtggcgacc | 900 |
| atcctccaaa atcggatctg gaagttctgt tccaggggcc cctgggatct catcaccatc | 960 |
| accatcacgg atccccggaa ttccccgggg tcgacctcga g gga aag cca ata cct | 1016 |
|                                                                  Gly Lys Pro Ile Pro<br>                                                                  1                 5 | |
| aat cca cta ctt gga cta gaa tcc aca taggcggccg caatcgtgac<br>Asn Pro Leu Leu Gly Leu Glu Ser Thr<br>                   10 | 1063 |
| tgactgacga tctgcctcgc gcgtttcggt gatgacggtg aaaacctctg acacatgcag | 1123 |
| ctcccggaga cggtcacagc ttgtctgtaa gcggatgccg ggagcagaca gcccgtcag | 1183 |
| ggcgcgtcag cgggtgttgg cgggtgtcgg ggcgcagcca tgacccagtc acgtagcgat | 1243 |
| agcggagtgt ataattcttg aagacgaaag ggcctcgtga tacgcctatt tttataggtt | 1303 |
| aatgtcatga taataatggt ttcttagacg tcaggtggca cttttcgggg aaatgtgcgc | 1363 |
| ggaacccta tttgtttatt tttctaaata cattcaaata tgtatccgct catgagacaa | 1423 |
| taaccctgat aaatgcttca ataatattga aaaggaaga gtatgagtat tcaacatttc | 1483 |

```
cgtgtcgccc ttattcccctt ttttgcggca ttttgccttc ctgttttgc tcacccagaa    1543 acgctggtga aagtaaaaga tgctgaagat cagttgggtg cacgagtggg ttacatcgaa    1603
ctggatctca acagcggtaa gatccttgag agttttcgcc ccgaagaacg ttttccaatg    1663
atgagcactt ttaaagttct gctatgtggc gcggtattat cccgtgttga cgccgggcaa    1723
gagcaactcg gtcgccgcat acactattct cagaatgact tggttgagta ctcaccagtc    1783
acagaaaagc atcttacgga tggcatgaca gtaagagaat tatgcagtgc tgccataacc    1843
atgagtgata acactgcggc caacttactt ctgacaacga tcggaggacc gaaggagcta    1903
accgcttttt tgcacaacat gggggatcat gtaactcgcc ttgatcgttg gaaccggag    1963 ctgaatgaag ccataccaaa cgacgagcgt gacaccacga tgcctgcagc aatggcaaca    2023
acgttgcgca aactattaac tggcgaacta cttactctag cttcccggca acaattaata    2083
gactggatgg aggcggataa agttgcagga ccacttctgc gctcggccct tccggctggc    2143
tggtttattg ctgataaatc tggagccggt gagcgtgggt ctcgcggtat cattgcagca    2203
ctggggccag atggtaagcc ctcccgtatc gtagttatct acacgacggg gagtcaggca    2263
actatggatg aacgaaatag acagatcgct gagataggtg cctcactgat taagcattgg    2323
taactgtcag accaagttta ctcatatata ctttagattg atttaaaact tcatttttaa    2383
tttaaaagga tctaggtgaa gatccttttt gataatctca tgaccaaaat cccttaacgt    2443
gagttttcgt tccactgagc gtcagacccc gtagaaaaga tcaaaggatc ttcttgagat    2503 ccttttttc tgcgcgtaat ctgctgcttg caaacaaaaa aaccaccgct accagcggtg    2563
gtttgtttgc cggatcaaga gctaccaact ctttttccga aggtaactgg cttcagcaga    2623
gcgcagatac caaatactgt ccttctagtg tagccgtagt taggccacca cttcaagaac    2683
tctgtagcac cgcctacata cctcgctctg ctaatcctgt taccagtggc tgctgccagt    2743
ggcgataagt cgtgtcttac cgggttggac tcaagacgat agttaccgga taaggcgcag    2803
cggtcgggct gaacggggggg ttcgtgcaca gcccagct tggagcgaac gacctacacc    2863
gaactgagat acctacagcg tgagctatga aaagcgcca cgcttcccga agggagaaag    2923
gcggacaggt atccggtaag cggcagggtc ggaacaggag agcgcacgag ggagcttcca    2983
gggggaaacg cctggtatct ttatagtcct gtcgggtttc gccacctctg acttgagcgt    3043
cgatttttgt gatgctcgtc aggggggcgg agcctatgga aaaacgccag caacgcggcc    3103 ttttttacggt tcctggcctt ttgctggcct tttgctcaca tgttctttcc tgcgttatcc    3163
cctgattctg tggataaccg tattaccgcc tttgagtgag ctgataccgc tcgccgcagc    3223
cgaacgaccg agcgcagcga gtcagtgagc gaggaagcgg aagagcgcct gatgcggtat    3283
tttctcctta cgcatctgtg cggtatttca caccgcataa attccgacac catcgaatgg    3343
tgcaaaacct ttcgcggtat ggcatgatag cgcccggaag agagtcaatt cagggtggtg    3403
aatgtgaaac cagtaacgtt atacgatgtc gcagagtatg ccggtgtctc ttatcagacc    3463
gtttcccgcg tggtgaacca ggccagccac gtttctgcga aaacgcggga aaaagtggaa    3523
gcggcgatgg cggagctgaa ttacattccc aaccgcgtgg cacaacaact ggcgggcaaa    3583
cagtcgttgc tgattggcgt tgccacctcc agtctggccc tgcacgcgcc gtcgcaaatt    3643
gtcgcggcga ttaaatctcg cgccgatcaa ctgggtgcca gcgtggtggt gtcgatggta    3703
gaacgaagcg gcgtcgaagc ctgtaaagcg gcggtgcaca atcttctcgc gcaacgcgtc    3763
agtgggctga tcattaacta tccgctggat gaccaggatg ccattgctgt ggaagctgcc    3823
tgcactaatg ttccggcgtt atttcttgat gtctctgacc agacacccat caacagtatt    3883
```

```
atttctctccc atgaagacgg tacgcgactg ggcgtggagc atctggtcgc attgggtcac    3943
cagcaaatcg cgctgttagc gggcccatta agttctgtct cggcgcgtct gcgtctggct    4003
ggctggcata aatatctcac tcgcaatcaa attcagccga tagcggaacg ggaaggcgac    4063
tggagtgcca tgtccggttt tcaacaaacc atgcaaatgc tgaatgaggg catcgttccc    4123
actgcgatgc tggttgccaa cgatcagatg gcgctgggcg caatgcgcgc cattaccgag    4183
tccgggctgc gcgttggtgc ggatatctcg gtagtgggat acgacgatac cgaagacagc    4243
tcatgttata tcccgccgtc aaccaccatc aaacaggatt ttcgcctgct ggggcaaacc    4303
agcgtggacc gcttgctgca actctctcag ggccaggcgg tgaagggcaa tcagctgttg    4363
cccgtctcac tggtgaaaag aaaaaccacc ctggcgccca atacgcaaac cgcctctccc    4423
cgcgcgttgg ccgattcatt aatgcagctg gcacgacagg tttcccgact ggaaagcggg    4483
cagtgagcgc aacgcaatta atgtgagtta gctcactcat taggcacccc aggctttaca    4543
ctttatgctt ccggctcgta tgttgtgtgg aattgtgagc ggataacaat ttcacacagg    4603
aaacagctat gaccatgatt acggattcac tggccgtcgt tttacaacgt cgtgactggg    4663
aaaaccctgg cgttacccaa cttaatcgcc ttgcagcaca tccccctttc gccagctggc    4723
gtaatagcga agaggcccgc accgatcgcc cttcccaaca gttgcgcagc ctgaatggcg    4783
aatggcgctt tgcctggttt ccggcaccag aagcggtgcc ggaaagctgg ctggagtgcg    4843
atcttcctga ggccgatact gtcgtcgtcc cctcaaactg gcagatgcac ggttacgatg    4903
cgcccatcta caccaacgta acctatccca ttacggtcaa tccgccgttt gttcccacgg    4963
agaatccgac gggttgttac tcgctcacat ttaatgttga tgaaagctgg ctacaggaag    5023
gccagacgcg aattattttt gatggcgttg gaatt                               5058
```

```
<210> SEQ ID NO 6
<211> LENGTH: 288
<212> TYPE: DNA
<213> ORGANISM: Homo sapiens
<220> FEATURE:
<221> NAME/KEY: CDS
<222> LOCATION: (1)..(288)
<223> OTHER INFORMATION: TSIM1 or SUBE1
<220> FEATURE:
<221> NAME/KEY: misc_feature
<222> LOCATION: (7)..(24)
<223> OTHER INFORMATION: natural linker of RNF4
<220> FEATURE:
<221> NAME/KEY: misc_feature
<222> LOCATION: (25)..(36)
<223> OTHER INFORMATION: SIM2 domain
<220> FEATURE:
<221> NAME/KEY: misc_feature
<222> LOCATION: (37)..(60)
<223> OTHER INFORMATION: natural linker of RNF4
<220> FEATURE:
<221> NAME/KEY: misc_feature
<222> LOCATION: (61)..(72)
<223> OTHER INFORMATION: SIM3 domain
<220> FEATURE:
<221> NAME/KEY: misc_feature
<222> LOCATION: (79)..(96)
<223> OTHER INFORMATION: natural linker of RNF4
<220> FEATURE:
<221> NAME/KEY: misc_feature
<222> LOCATION: (97)..(108)
<223> OTHER INFORMATION: SIM2 domain
<220> FEATURE:
<221> NAME/KEY: misc_feature
<222> LOCATION: (109)..(132)
<223> OTHER INFORMATION: natural linker of RNF4
<220> FEATURE:
```

-continued

```
<221> NAME/KEY: misc_feature
<222> LOCATION: (133)..(144)
<223> OTHER INFORMATION: SIM3 domain
<220> FEATURE:
<221> NAME/KEY: misc_feature
<222> LOCATION: (151)..(168)
<223> OTHER INFORMATION: natural linker of RNF4
<220> FEATURE:
<221> NAME/KEY: misc_feature
<222> LOCATION: (169)..(180)
<223> OTHER INFORMATION: SIM2 domain
<220> FEATURE:
<221> NAME/KEY: misc_feature
<222> LOCATION: (181)..(204)
<223> OTHER INFORMATION: natural linker of RNF4
<220> FEATURE:
<221> NAME/KEY: misc_feature
<222> LOCATION: (205)..(216)
<223> OTHER INFORMATION: SIM3 domain
<220> FEATURE:
<221> NAME/KEY: misc_feature
<222> LOCATION: (223)..(240)
<223> OTHER INFORMATION: natural linker of RNF4
<220> FEATURE:
<221> NAME/KEY: misc_feature
<222> LOCATION: (241)..(253)
<223> OTHER INFORMATION: SIM2 domain
<220> FEATURE:
<221> NAME/KEY: misc_feature
<222> LOCATION: (253)..(276)
<223> OTHER INFORMATION: natural linker of RNF4
<220> FEATURE:
<221> NAME/KEY: misc_feature
<222> LOCATION: (277)..(288)
<223> OTHER INFORMATION: SIM3 domain

<400> SEQUENCE: 6 gga tct gaa act gct gga gat gaa att gtg gac ctc act tgt gaa tct      48
Gly Ser Glu Thr Ala Gly Asp Glu Ile Val Asp Leu Thr Cys Glu Ser
1               5                   10                  15 tta gag cct gtg gtg gtt gat ctg gga tct gaa act gct gga gat gaa      96
Leu Glu Pro Val Val Val Asp Leu Gly Ser Glu Thr Ala Gly Asp Glu
            20                  25                  30 att gtg gac ctc act tgt gaa tct tta gag cct gtg gtg gtt gat ctg     144
Ile Val Asp Leu Thr Cys Glu Ser Leu Glu Pro Val Val Val Asp Leu
        35                  40                  45 gga tct gaa act gct gga gat gaa att gtg gac ctc act tgt gaa tct     192
Gly Ser Glu Thr Ala Gly Asp Glu Ile Val Asp Leu Thr Cys Glu Ser
50                  55                  60 tta gag cct gtg gtg gtt gat ctg gga tct gaa act gct gga gat gaa     240
Leu Glu Pro Val Val Val Asp Leu Gly Ser Glu Thr Ala Gly Asp Glu
65                  70                  75                  80 att gtg gac ctc act tgt gaa tct tta gag cct gtg gtg gtt gat ctg     288
Ile Val Asp Leu Thr Cys Glu Ser Leu Glu Pro Val Val Val Asp Leu
            85                  90                  95

<210> SEQ ID NO 7
<211> LENGTH: 96
<212> TYPE: PRT
<213> ORGANISM: Homo sapiens

<400> SEQUENCE: 7

Gly Ser Glu Thr Ala Gly Asp Glu Ile Val Asp Leu Thr Cys Glu Ser
1               5                   10                  15

Leu Glu Pro Val Val Val Asp Leu Gly Ser Glu Thr Ala Gly Asp Glu
            20                  25                  30

Ile Val Asp Leu Thr Cys Glu Ser Leu Glu Pro Val Val Val Asp Leu
        35                  40                  45
```

```
Gly Ser Glu Thr Ala Gly Asp Glu Ile Val Asp Leu Thr Cys Glu Ser
 50                  55                  60

Leu Glu Pro Val Val Asp Leu Gly Ser Thr Ala Gly Asp Glu
 65                  70                  75                  80

Ile Val Asp Leu Thr Cys Glu Ser Leu Glu Pro Val Val Asp Leu
                 85                  90                  95

<210> SEQ ID NO 8
<211> LENGTH: 288
<212> TYPE: DNA
<213> ORGANISM: Homo sapiens
<220> FEATURE:
<221> NAME/KEY: CDS
<222> LOCATION: (1)..(288)
<223> OTHER INFORMATION: TSIM2 or SUBE2
<220> FEATURE:
<221> NAME/KEY: misc_feature
<222> LOCATION: (7)..(27)
<223> OTHER INFORMATION: Artificial poly-glycine linker
<220> FEATURE:
<221> NAME/KEY: misc_feature
<222> LOCATION: (28)..(29)
<223> OTHER INFORMATION: SIM2 domain
<220> FEATURE:
<221> NAME/KEY: misc_feature
<222> LOCATION: (40)..(57)
<223> OTHER INFORMATION: Artificial poly-glycine linker
<220> FEATURE:
<221> NAME/KEY: misc_feature
<222> LOCATION: (58)..(72)
<223> OTHER INFORMATION: SIM3 domain
<220> FEATURE:
<221> NAME/KEY: misc_feature
<222> LOCATION: (79)..(99)
<223> OTHER INFORMATION: Artificial poly-glycine linker
<220> FEATURE:
<221> NAME/KEY: misc_feature
<222> LOCATION: (100)..(111)
<223> OTHER INFORMATION: SIM2 domain
<220> FEATURE:
<221> NAME/KEY: misc_feature
<222> LOCATION: (112)..(129)
<223> OTHER INFORMATION: Artificial poly-glycine linker
<220> FEATURE:
<221> NAME/KEY: misc_feature
<222> LOCATION: (130)..(144)
<223> OTHER INFORMATION: SIM3 domain
<220> FEATURE:
<221> NAME/KEY: misc_feature
<222> LOCATION: (151)..(171)
<223> OTHER INFORMATION: Artificial poly-glycine linker
<220> FEATURE:
<221> NAME/KEY: misc_feature
<222> LOCATION: (172)..(183)
<223> OTHER INFORMATION: SIM2 domain
<220> FEATURE:
<221> NAME/KEY: misc_feature
<222> LOCATION: (184)..(204)
<223> OTHER INFORMATION: Artificial poly-glycine linker
<220> FEATURE:
<221> NAME/KEY: misc_feature
<222> LOCATION: (205)..(216)
<223> OTHER INFORMATION: SIM3 Domain
<220> FEATURE:
<221> NAME/KEY: misc_feature
<222> LOCATION: (216)..(236)
<223> OTHER INFORMATION: Artificial poly-glycine linker
<220> FEATURE:
<221> NAME/KEY: misc_feature
<222> LOCATION: (223)..(243)
<223> OTHER INFORMATION: Artificial poly-glycine linker
<220> FEATURE:
<221> NAME/KEY: misc_feature
<222> LOCATION: (237)..(248)
<223> OTHER INFORMATION: SIM3 domain
<220> FEATURE:
```

```
<221> NAME/KEY: misc_feature
<222> LOCATION: (244)..(255)
<223> OTHER INFORMATION: SIM2 domain

<400> SEQUENCE: 8 gga tct ggc ggt gga gga ggc ggt ggg att gtg gac ctc ggt gga ggc     48
Gly Ser Gly Gly Gly Gly Gly Gly Ile Val Asp Leu Gly Gly Gly
1               5                   10                  15 gga ggg ggt gtc gtg gtt gat ctg gga tct ggc ggt gga gga ggc ggt     96
Gly Gly Gly Val Val Val Asp Leu Gly Ser Gly Gly Gly Gly Gly Gly
            20                  25                  30 ggg att gtg gac ctc ggt gga ggc gga ggg ggt gtc gtg gtt gat ctg    144
Gly Ile Val Asp Leu Gly Gly Gly Gly Gly Gly Val Val Val Asp Leu
        35                  40                  45 gga tct ggc ggt gga gga ggc ggt ggg att gtg gac ctc ggt gga ggc    192
Gly Ser Gly Gly Gly Gly Gly Gly Ile Val Asp Leu Gly Gly Gly
50                  55                  60 gga ggg ggt gtc gtg gtt gat ctg gga tct ggc ggt gga gga ggc ggt    240
Gly Gly Gly Val Val Val Asp Leu Gly Ser Gly Gly Gly Gly Gly Gly
65                  70                  75                  80 ggg att gtg gac ctc ggt gga ggc gga ggg ggt gtc gtg gtt gat ctg    288
Gly Ile Val Asp Leu Gly Gly Gly Gly Gly Gly Val Val Val Asp Leu
        85                  90                  95

<210> SEQ ID NO 9
<211> LENGTH: 96
<212> TYPE: PRT
<213> ORGANISM: Homo sapiens

<400> SEQUENCE: 9

Gly Ser Gly Gly Gly Gly Gly Gly Ile Val Asp Leu Gly Gly Gly
1               5                   10                  15

Gly Gly Gly Val Val Val Asp Leu Gly Ser Gly Gly Gly Gly Gly Gly
            20                  25                  30

Gly Ile Val Asp Leu Gly Gly Gly Gly Gly Gly Val Val Val Asp Leu
        35                  40                  45

Gly Ser Gly Gly Gly Gly Gly Gly Ile Val Asp Leu Gly Gly Gly
    50                  55                  60

Gly Gly Gly Val Val Val Asp Leu Gly Ser Gly Gly Gly Gly Gly Gly
65                  70                  75                  80

Gly Ile Val Asp Leu Gly Gly Gly Gly Gly Val Val Val Asp Leu
        85                  90                  95

<210> SEQ ID NO 10
<211> LENGTH: 12
<212> TYPE: DNA
<213> ORGANISM: Homo sapiens
<220> FEATURE:
<221> NAME/KEY: CDS
<222> LOCATION: (1)..(12)
<223> OTHER INFORMATION: SIM2 domain

<400> SEQUENCE: 10 att gtg gac ctc                                                     12
Ile Val Asp Leu
1

<210> SEQ ID NO 11
<211> LENGTH: 4
<212> TYPE: PRT
<213> ORGANISM: Homo sapiens

<400> SEQUENCE: 11
```

```
Ile Val Asp Leu
1

<210> SEQ ID NO 12
<211> LENGTH: 12
<212> TYPE: DNA
<213> ORGANISM: Homo sapiens
<220> FEATURE:
<221> NAME/KEY: CDS
<222> LOCATION: (1)..(12)
<223> OTHER INFORMATION: SIM3 domain

<400> SEQUENCE: 12 gtg gtt gat ctg                                                        12
Val Val Asp Leu
1

<210> SEQ ID NO 13
<211> LENGTH: 4
<212> TYPE: PRT
<213> ORGANISM: Homo sapiens

<400> SEQUENCE: 13

Val Val Asp Leu
1
```

HIGH AFFINITY SUMO TRAPS

CROSS-REFERENCE TO RELATED APPLICATIONS

This application is filed under the provisions of 35 U.S.C. §371 and claims the priority of International Patent Application No. PCT/EP2012/054039 filed on 8 Mar. 2012 entitled "HIGH AFFINITY SUMO TRAPS" in the name of Manuel Salvador RODRÍGUEZ MEDINA, which claims priority to U.S. Provisional Patent Application No. 61/489,490, filed on 24 May 2011, both of which are hereby incorporated by reference herein in their entirety.

FIELD OF THE INVENTION

The invention relates to the field of purification of target proteins based on their affinity towards specific binding reagents. In particular, the invention relates to methods for the purification by affinity binding of SUMO (Small-ubiquitin modifier) and SUMO-conjugate proteins by the use of fusion proteins comprising tandem arrangements of SUMO interacting motifs.

BACKGROUND OF THE INVENTION

The post-translational modifications of proteins with proteins of the ubiquitin family are highly dynamic processes that increase the potential of the cell to adapt to multiple physiological or pathological situations (Hayashi et al., 2002; Seufert et al., 1995). Modification of proteins by the small ubiquitin modifier (SUMO) results in very diverse outcomes. The first identified targets of SUMO, the oncogenic protein PML (promyelocytic leukemia) and the nucleocytoplasmatic transport protein RanGAP1 (RanGTPase-activating1), allowed to connect SUMO functions to nuclear localization (Matunis et al., 1996; Lapenta et al., 1997; Mahajan et al. 1997; Wilkinson and Henley, 2010). The identification and characterization of hundreds of SUMO substrates suggest the role of SUMO as regulator of protein activity and stability (Seeler and Dejean, 2003). Downstream consequences are mediated, at least in part, by effectors that contain SUMO-interacting motifs or SIMs.

SUMO proteins only have a 20% of identity with ubiquitin, however, have a similar three-dimensional structure (Kerscher et al., 2006) (FIG. 1). Three forms of SUMO (SUMO-1, SUMO-2 and SUMO-3) are ubiquitously expressed and migrate with an apparent molecular weight of around 10 kDa in a denaturing polyacrylamide gel. SUMO-1 shares only 50% of identity with SUMO-2 and SUMO-3, but SUMO-2 and SUMO-3 are 97% identical, and form a distinct subfamily known as SUMO 2/3 (Tatham et al., 2001).

As it occurs with ubiquitin, SUMO molecules are generated through the processing of a high molecular weight precursor, the cleavage of which exposes the double glycine signature that is involved in their conjugation to protein substrates. A thiol-esther cascade of 3 reactions mediates the conjugation of SUMO molecules (FIG. 2). A single SUMO activating enzyme (SAE) or E1, activate all SUMO molecules that are conjugated by the E2 Ubc9 (Hay, 2005; Wilkinson and Henley, 2010).

This process is facilitated by a specific SUMO E3 ligase. SUMO E3 ligases, such as members of the PIAS (protein inhibitor of activated STAT) family and RanBP3 (Ran-binding protein 3), contain a SP-RING (Really Interesting New Gene) motif which is essential for their function (Kahyo et al., 2001 Schmidt and Muller, 2002). A distinct group of SUMO-ligases is composed by Polycom protein (Pc2) which is associated to gene silencing (Kagey et al., 2003). SUMOylation is a highly reversible modification that is mediated by SUMO specific cystein proteases (SUSPs or SENPs). In mammals 6 SENPs were initially reported, of which SENP1-SENP3 and SENP5-SENP7 are specific for SUMO proteins. The localization of SENPs and specificity for SUMO-isoforms determines their action (Yeh, 2009). The initial mapping of SUMO modification lysine residues allowed the identification of a SUMO consensus site composed by ψKxE, in which Ψ is a large hydrophobic aminoacid and x any aminoacid (Rodriguez et al., 2001; Xu et al., 2008). Such consensus was found in RanGAP1, PML, p53 and IκBα, among other proteins and interacts directly with Ubc9 (Sampson et al., 2001; Wilkinson and Henley, 2010). The target lysine enters into the catalytic pocket of Ubc9 whereas the hydrophobic and acidic residues interact with the surface of this E2 (Bernier-Villamor et al., 2002). Although, not all SUMOylation sites fit with the canonical consensus, modification will only occur if the consensus presents an unstructured region or a well exposed substrate surface (Geiss-Friedlander and Melchior, 2007).

The stimulation of SUMO proteins to their substrates could be reached by cellular stress, such heat shock. Golebiowski and colleagues (Golebiowski, 2009) described a quantitative change in global SUMOylation profiles during heat shock, because previous experiments demonstrated a rapid and reversible increase in SUMO-2 and SUMO-3 conjugates when cells were shifted from the normal growth temperature of 37° C. to the stressful 43° C. (Saitoh and Hinchey, 2000).

The consequences of the SUMOylation of a new protein target are difficult to predict as the changes of conformation, creation or masking interaction surfaces may affect activity, stability and localization of modified proteins. SUMOylated proteins are recognized by SUMO interacting motifs (SIMs) present in a large diversity of proteins including promyelocytic leukemia (PML), death domain-associated protein (Daxx), ubiquitin-like modifier activating enzyme 2 (UBA2), protein inhibitors of activated STAT (PIAS) and RING finger protein 4 (RNF4) ligases (Geiss Friedlander and Melchior 2007). SIMs contain a hydrophobic core flanked by acidic (E/D) and a serine residues (Song et al., 2004; Hecker et al., 2006). SIM motifs form a β-strand that bind in parallel or anti-parallel orientation between the α-helix and a βstrand of SUMO (FIG. 3).

The affinity of SIM and SUMO usually is low, around the high micromolar range, which is normally due to the reduced surface of interaction. To increase such affinity, proteins such as the SUMO-dependent ubiquitin ligase RNF4 contain 4 SIM domains. SIM2 and SIM3 appear to play a more important role in the capture of SUMOylated proteins (Tatham et al., 2008). In this way SUMOylated PML is targeted to degradation by the ubiquitin-proteasome system, providing the first molecular evidence about how SUMO molecules can contribute to regulate protein stability. Affinity columns containing 4 SIMs derived form natural occurring fragment 32-133 of RNF4 have been published (Bruderer R et al. 2011) and commercialized by BIOMOL (Affinity research).

DESCRIPTION OF THE INVENTION

Brief Description of the Invention

Based on the observation that the RNF4 protein natural (GeneBank ID: 6047) contains more than one SIM, the present invention generates proteins with additional SUMO affinity motifs. These engineered proteins should increase the affinity of individual SIMs to interact with SUMO-modified targets, allowing the study of post-modification mechanisms that connect signaling cascades with effectors functions. According with the resolved and published molecular structures for SUMO and SIM domains (FIG. 3), a cooperative interaction between SUMO molecules and these SUMO traps designed in present invention was expected. This invention shows that polypeptides disclosed in the present invention, hereinafter referred to Tandem SUMO Interacting Motifs (TSIM) or SUMO-Binding Entities (SUBEs) indistinctly, expressing more than four SIMs arranged in tandem, preferably, at least, eight SIMs arranged in tandem. These SIMs in tandem can be efficiently used to capture and analyse SUMOylated proteins in vitro and/or ex-vivo. Furthermore, TSIMs of present invention show higher capacity to purify SUMOylated proteins.

According to the invention, the term "in vitro" refers to a biological processes or reactions that are conducted using components of an organism that have been isolated from their usual biological context in order to permit a more detailed or more convenient analysis than can be done with whole organisms, in an artificial environment, i.e. a laboratory.

According to the invention, the term "ex vivo" refers to a process that which takes place outside an organism. Particularly, this term refers to experimentation or measurements done in or on sample or tissue in an artificial environment outside the organism with the minimum alteration of natural conditions. Samples or tissues can be removed by any method known and used for the same purpose in the state of the art.

According to the invention, the term "tandem" refers to the existence in the same DNA or protein sequence, of at least two or more different fragments (nucleotides or amino acids), close to each other but separated by linkers or spacers, in alternance. Particularly, in the present invention, the tandem term refers to more than four repetitions of SIMs, preferably at least, eight repetitions of SIMs, more preferably four repetitions of SIM2 (SEQ ID NO: 10) and four repetitions of SIM3 (SEQ ID NO: 12), both sequences from RNF4 protein (GeneBank ID: 6047), that are arranged, alternatively SIM2-linker-SIM3-linker-SIM2-linker-SIM3-linker-SIM2-linker-SIM3-linker-SIM2-linker-SIM3, wherein the linkers are either natural or artificial linkers.

For the purpose of the present invention the term "comprise" or "comprising", all along present patent description, includes, specifically, the term "consisting" or "consisting of", when referred, particularly, to SUMO interacting motifs (SIMs) and to biological sequences. Thus, in a first aspect, the present invention refers to a polypeptide comprising more than four SUMO interacting motifs (SIM), wherein said SUMO interacting motifs are linked to each other by an artificial (non-natural) or by a natural amino acid sequence linker. Preferably, the SUMO interacting motifs are arranged in tandem and more preferably the polypeptide disclosed in the present invention comprising at least eight SUMO interacting motifs (SIM) arranged in tandem.

Thus, eight SIM motifs in tandem obtained by four repetitions of the SIM2 sequence (SEQ ID NO: 10) and SIM3 sequence (SEQ ID NO: 12) of RNF4 (GeneBank ID: 6047), we are arranged, spaced by either the natural linker or an artificial poly-glycine linker (FIG. 4). These constructs named TSIM1 or SUBE1 (SEQ ID NO:7) and TSIM2 or SUBE 2 (SEQ ID NO:9) respectively, were cloned into a GST protein expressing vector (pGEX6P1 SV5 His6) (SEQ ID NO:5). This protein allows the purification of the TSIMs or SUBEs through a Glutathione-Sepharose column (FIG. 5). In addition to the SIMs, this vector allows the expression of an N-terminus His6 tag and C-terminus epitope recognized by specific antibodies (FIG. 6). These tags are useful to verify the integrity of the traps by Western blot analysis and to consider further purification steps by immunoprecipitation, when required. Tags also allow immunodetection procedures (ELISA) and the study of sub-cellular distribution by indirect immunofluorescence. Another advantage of this construct is the possibility to use precision protease cleavage that removes the GST after incubation with this specific enzyme. Furthermore, the TSIM1 or SUBE1 (SEQ ID NO:7) contains natural linker, present in RNF4, between SIM sequences and TSIM2 or SUBE2 (SEQ ID NO:9) contains synthetic poly-glycine linkers between SIMs sequences. TSIM2 or SUBE2 thanks to synthetic poly-glycine linkers, may capture a wide spectrum of SUMOylated proteins. Moreover, traps combining TSIM1 (SUBE1) with TSIM2 (SUBE2), the spectrum of SUMOylated proteins to be detected and/or isolated increases with regard to the use of traps based on TSIM1 (SUBE1) or TSIM2 (SUBE2), independently.

In a second aspect, the invention refers to the use of a polypeptide according to the invention for the isolation of SUMOylated proteins.

In a further aspect, the invention refers to a nucleotide sequence encoding a polypeptide according to the invention.

In a further aspect, the invention refers to a gene construct comprising a nucleotide sequence according to the invention.

In a further aspect, the invention refers to an expression vector comprising a nucleotide sequence or a gene construct according to the invention.

In a further aspect, the invention refers to a cell comprising a nucleotide sequence, or a gene construct, or a vector according to the invention.

In a further aspect, the invention refers to a non-human animal comprising a nucleotide sequence, or a gene construct, or a vector, or a cell according to the present invention.

In a further aspect, the invention refers to a process for obtaining a polypeptide according to the present invention, which comprises culturing a cell according to the present invention under conditions which allow producing said polypeptide and, if desired, recovering said polypeptide from the culture medium.

In a further aspect, the invention refers to an in vitro method for the isolation of a SUMOylated protein from a sample which comprises
  i) incubating a polypeptide disclosed in the present invention with said sample in conditions allowing said polypeptide to interact with said SUMOylated protein present in said sample; and
  ii) recovering said SUMOylated protein which is bound to said polypeptide.

In a last aspect, the invention refers to a kit including a diagnosis kit, comprising a polypeptide according to the present invention, for detection/isolation of sumoylated proteins.

DESCRIPTION OF THE FIGURES

FIG. 4: Structure, DNA and aminoacid sequence of the SUMO traps (TSIMs). The two types of SUMO traps contain SIM domains 2 and 3 of RNF4 protein (underlined) and are spaced by either the natural linkers (TSIM1 or SUBE1) or artificial linkers (TSIM2 or SUBE2).

FIG. 5: Scheme strategy for the preparation, purification and detection of TSIMs SUMO-traps. Top part illustrates the steps of purification of TSIMs to be used as affinity columns.

DETAILED DESCRIPTION OF THE INVENTION

Figure 1:
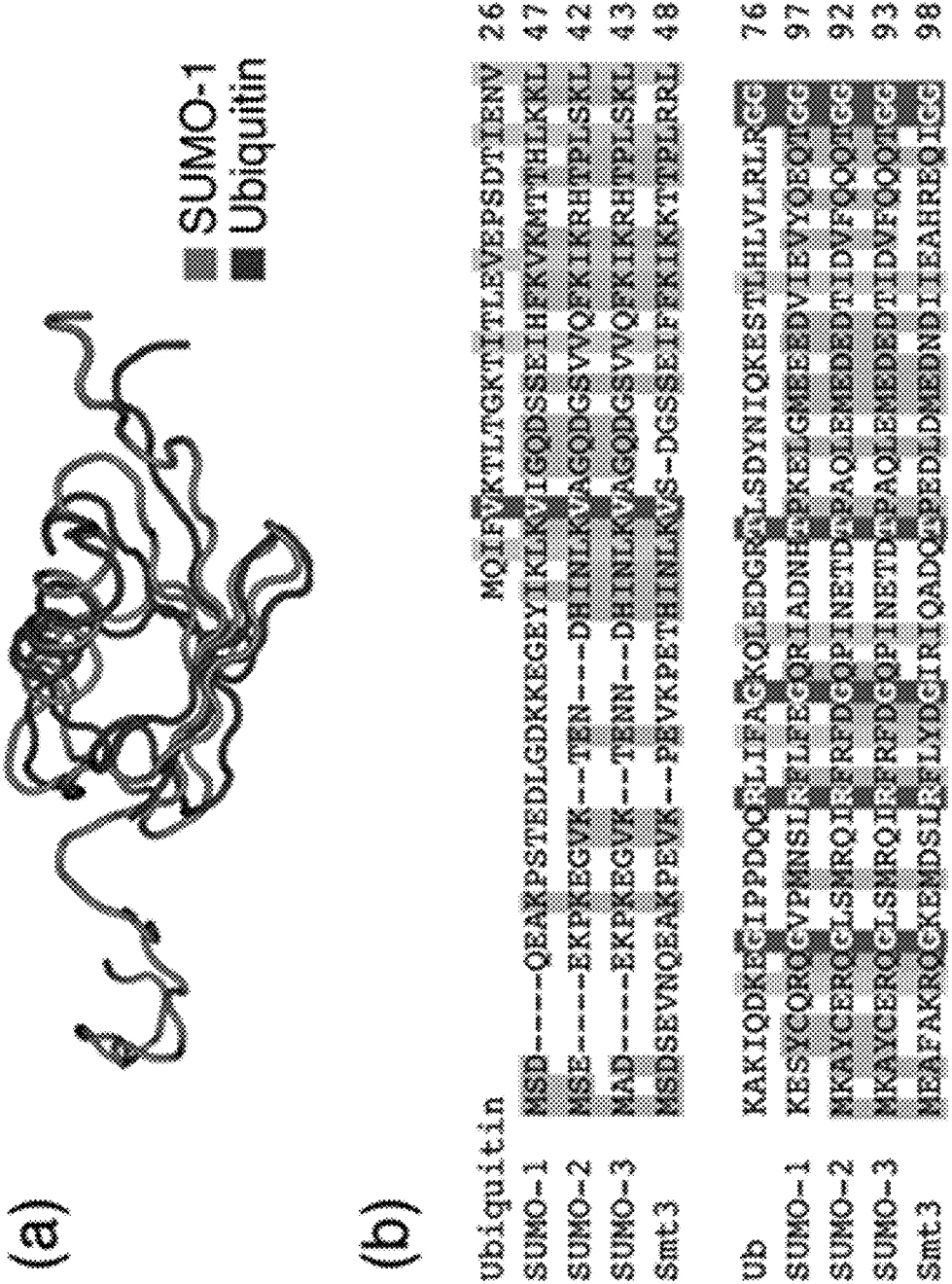
FIG. 1: Comparison of SUMO and ubiquitin. (a) Structural alignment of the backbones of SUMO-1 (grey) and ubiquitin (black) from the VAST database (NCBI). (b) Sequence alignment of H. sapiens ubiquitin (Ub), SUMO-1, SUMO-2, and SUMO-3 and the *S. cerevisiae* SUMO protein Smt3 was made using ClustalW (http://www.ebi.ac.uk/Tools/msa/clustalw2/). Positions that are identical in all sequences are shaded dark, and conserved positions are enclosed in squared. Positions that are identical in at least three of the SUMO proteins, but not in Ub, are shaded grey (Jonhson, 2004).
Figure 2:
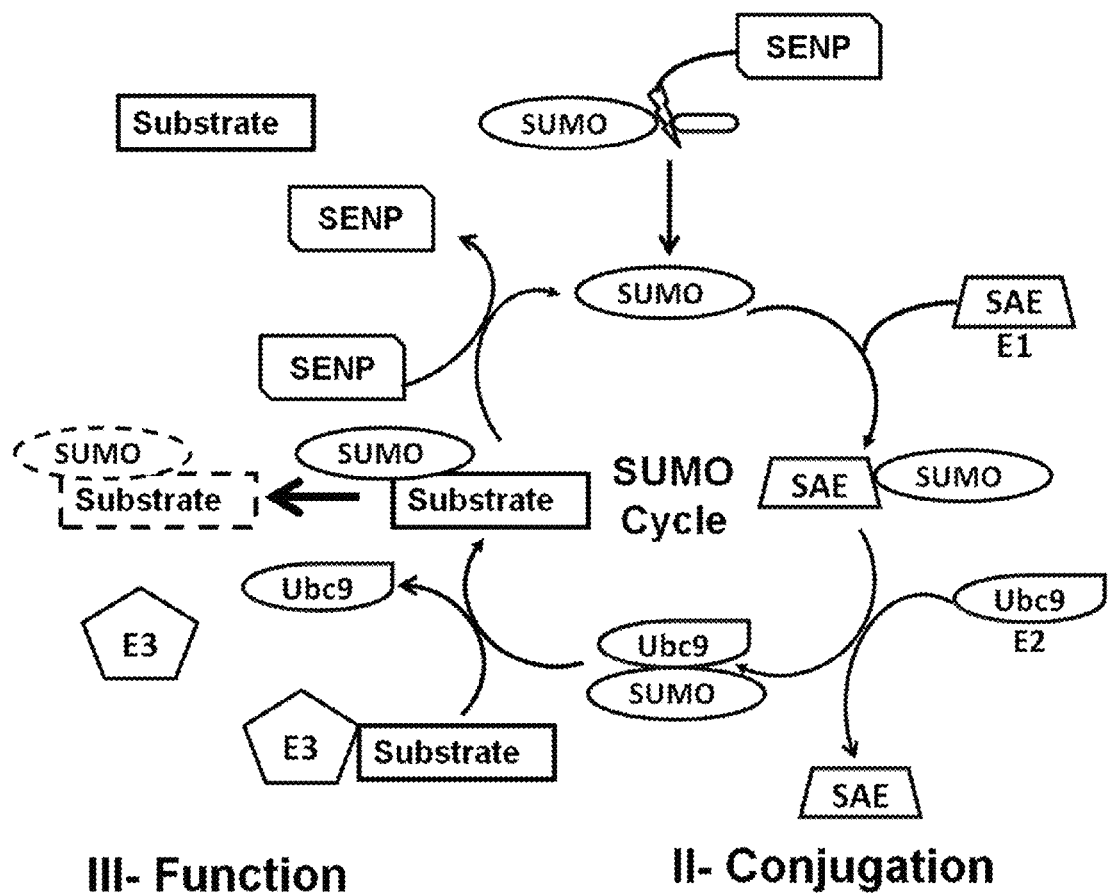
FIG. 2: SUMO cycle. The conjugation of SUMO is mediated by the SUMO activating enzyme (SAE) or E1 and the conjugating enzyme (E2) Ubc9. E3 SUMO-ligases are diverse and specific for each reaction. Maturation and recycling of SUMO molecules is mediated by SUMO specific cystein proteases (SENP). SUMO-modified substrates connect with multiple functions.
Figure 3:
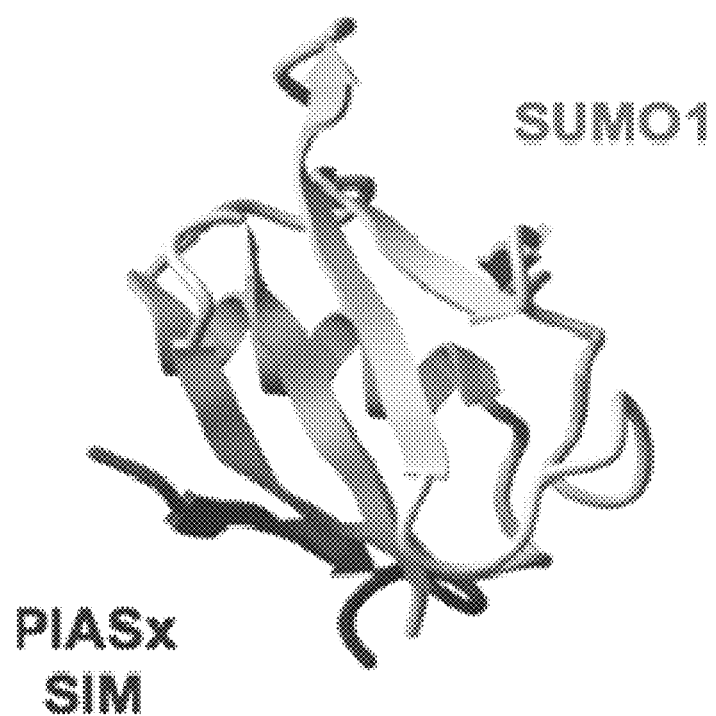
FIG. 3: Model of SUMO structure and interaction with SIMs. Ribbon structure of the SIM of PIASx bound to the SUMO1 molecule according to the published structure PDB: 2ASQ (Miteva et al., 2010).
Figure 6:
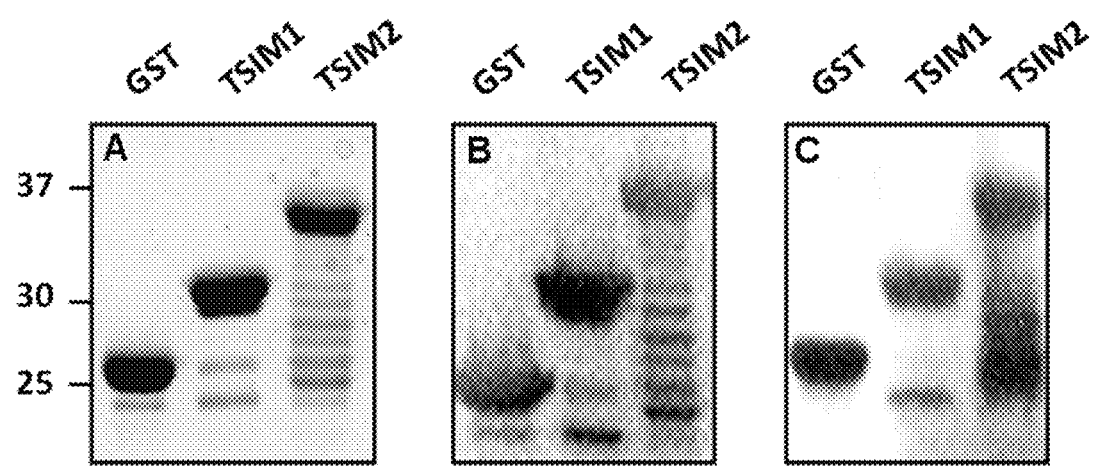
FIG. 6: Detection of TSIMs SUMO-traps. Detection of purified proteins GST, TSIM1 (SUBE1) and TSIM2 (SUBE2) detected by A) Coomassie blue, B) by Western-blot with anti-GST and C) anti-SV5 antibodies. Numbers to the left of the photographs indicate the molecular weight marker.

Present invention relates to the role of protein SUMOylation in the control of multiple vital processes, particularly to the potential use of SIMs to isolate SUMOylated targets. The invention has achieved an increase of the affinity for SUMOylated proteins by artificially arranging SIMs in tandem (TSIMs or SUBEs). The invention has used SIM2 (SEQ ID NO: 10) and SIM3 (SEQ ID NO: 12) of RNF4 as they show higher capacity to interact with SUMOylated proteins (Tatham et al., 2008). Using the natural tandem of SIM2 and SIM3 of the SUMO-dependent ubiquitin ligase RNF4, it has been multiplied to up to 4 times this sequence to obtain eight SIMs arranged in tandem in each SUMO-trap. DNA encoding such motifs were cloned one after the other in a 5'-3' oriented manner. A first embodiment is related to a TSIM (SUBE) version called TSIM1 (SUBE1) (SEQ ID NO: 6), which keep the natural linkers present in RNF4 whereas a second embodiment contains an artificial poly glycine linker and is called TSIM2 (SUBE2) (SEQ ID NO: 8) (FIG. 4). The flexibility of the artificial linkers introduced into the TSIM2 (SUBE2) increases its capacity to capture a broader range of SUMOylated proteins not specially related to RFN4. Furthermore, the invention demonstrates that TSIMs (SUBEs) can be used to study SUMO-regulated processes under different cellular stress situations. Therefore, TSIMs (SUBEs) according to present invention are useful molecular tools to capture and identify polySUMOylated proteins from cell extracts and from in vitro assays.

Thus, the present invention refers to a polypeptide comprising more than four SUMO interacting motifs (SIM), wherein said SUMO interacting motifs are linked to each other by an artificial or by a natural amino acid sequence linker. Preferably, the SUMO interacting motifs (SIM) are arranged in tandem.

In a particular embodiment of the present invention, the polypeptide comprising at least eight SUMO interacting motifs (SIM) arranged in tandem, wherein said SUMO interacting motifs are linked to each other by an artificial or by a natural amino acid sequence linker.

SUMO interacting motif can be defined as segmented portions of a polypeptide sequence which recognizes and interacts with SUMOylated proteins. In a particular embodiment of the invention, said SUMO interacting motif is selected from the group of proteins that present such motifs which comprises, among other: PML (Promyelocytic leukemia protein), Daxx (death-domain associated protein), UBA2 (ubiquitin-like modifier activating enzyme 2), PIAS (protein inhibitor of activated STAT), RNF4 (ring finger protein 4) ligase and/or functionally equivalents variants thereof. In a preferred embodiment of the invention, said SUMO interacting motif is selected from the group comprising an SIM1, SIM2, SIM3, SIM4 and/or combinations thereof. In a more preferred embodiment, SUMO interacting motifs are the SIM2 (SEQ ID NO: 10) and/or SIM3 (SEQ ID NO: 12) from the RNF4 ligase protein (GeneBank ID: 6047) or functionally equivalent variants thereof.

The term "functionally equivalent" as used herein refers to a polypeptide according to the invention that preferably retains at least one biological function or activity of the specific amino acid sequence of a SUMO interacting motif, preferable the ability to bind to SUMO or to a SUMOylated protein.

In another particular embodiment of the invention, the polypeptide of the invention comprises four SIM2 motifs and four SIM3 motifs and/or functionally equivalent variants thereof. In another preferred embodiment of the invention, said polypeptide is selected from the group comprising SEQ ID NO: 7 and/or SEQ ID NO: 9.

As mentioned above, in a particular embodiment, the polypeptide of the invention comprises at least eight SUMO interacting motifs arranged in tandem which are linked to each other via artificial or by natural amino acid sequence linker.

According to the invention, the term "linker or spacer" as used herein, refers to a region that provides space between the SUMO interacting motifs. Thereby it is ensured that the secondary structure of the SUMO interacting motif is not affected by the presence of the neighbouring SUMO interacting motif so that the function of the SUMO interacting motif is maintained. Preferably, the linker or spacer is of polypeptide nature. In this way the nucleic acid sequence encoding the linker can be inserted between the sequences encoding the SUMO interacting motif and the whole construct can be produced at the same time. The linker peptide preferably comprises at least two amino acids, such as at least three amino acids, for example at least five amino acids, such as at least ten amino acids, for example at least 15 amino acids, such as at least 20 amino acids, for example at least 30 amino acids, such as at least 40 amino acids, for example at least 50 amino acids, such as at least 60 amino acids, for example at least 70 amino acids, such as at least 80 amino acids, such as at least 90 amino acids such as approximately 100 amino acids. The linker or spacer may be linked to the flanking of SUMO interacting motif through covalent linkages and preferably the linker or spacer is essentially non-immunogenic, and/or is not prone to proteolytic cleavage, and/or does not comprise any cystein residues. The following are examples of linker sequences, which are believed to be especially preferable for linking SUMO interacting motif. Preferred examples of spacer or linker peptides include those which have been used to link proteins without substantially impairing the function of the linked proteins or at least without substantially impairing the function of one of the linked proteins. More preferably the linkers or spacers have been used to link proteins comprising coiled-coil structures.

According to the invention, the term "flexible linker or spacer" as used herein, refers to a sequence hinge region between SUMO interacting motifs, allowing them to move independently of one another while maintaining the three-dimensional shape of the individual domains. In that sense, a flexible sequence linker according to the invention would be a hinge region characterized by a structural softness that enables this motion.

According to the invention, the term "artificial (non-natural) linker or spacer" as used herein, refers to a peptide linker with a length of at least 2 amino acids. In a more preferred embodiment, the artificial peptide linker comprises 2 or more amino acids selected from the group consisting of glycine, serine, alanine and threonine. In a preferred embodiment of the invention, said artificial linker is a poly-glycine linker. In a more preferred embodiment to the invention, said artificial poly-glycine linker is a flexible linker.

According to the invention, the term "natural linker or spacer" as used herein, refers to a natural sequence present in naturally occurring proteins that present the SUMO interacting motif described in the present invention, including PML, Daxx, UBA-2, PIAS and RNF4. In a preferred embodiment of the invention, the natural linker is the linker presents in RNF4 protein.

In a particular embodiment of the invention, the polypeptides of the invention further comprise the amino acid sequence of a tag. Said tag includes but is not limited to: polyhistidine tags (His-tags) (for example H6 and H10, etc.) or other tags for use in Immobilised metal ion affinity chromatography (IMAC) systems, for example, Ni2+ affinity columns, etc., Glutathione 5-Transferase (GST) fusions, Maltose Binding Protein (MBP) fusions, streptavidine-tags, the BirA substrate peptide (BSP) biotinylation target sequence of the bacterial enzyme BirA and tag epitopes that are directed by antibodies (for example c-myc tags, FLAG-tags, among others). Said tag peptides can be used for purification, inspection, selection and/or visualization of the fusion protein of the invention. In a particular embodiment of the invention, said tag is a detection tag and/or a purification tag. Inventors have shown (see Example) that when the polypeptide of the invention comprises a N-terminal His6× tag and a C-terminal epitope, these can be recognised by specific antibodies allowing immunoprecipitation, immunodetection (ELISA and Western-blot) and sub-cellular distribution by indirect immunofluorescence. Hence, in a preferred embodiment of the invention, said detection tag is the Sv5 epitope tag and said purification tag is a polyhistidine tag.

Present invention relates not only to the specific amino acid sequences disclosed wherein, but also to variants thereof, specifically to functionally equivalent variants thereof, such as fragments, analogues and/or derivatives. Thus, a variant of a specific amino acid sequence preferably retains at least one biological function or activity of the specific amino acid sequence, preferable the ability to bind to SUMO or to a SUMOylated protein.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (iv) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to SUMO or to a SUMOylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm (BLAST Manual, Altschul, S., et al., NCBI NLM NIH Bethesda, Md. 20894, Altschul, S., et al., 1990).

The polypeptides of the invention can be post-translationally modified. For example, post-translational modifications that fall within the scope of the present invention include signal peptide cleavage, glycosylation, acetylation, isoprenylation, proteolysis myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include artificial amino acids formed by post-translational modification or by introducing artificial amino acids during translation. A variety of approaches are available for introducing artificial amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALYS), could be modified with an amine specific photoaffinity label.

As explained before, the polypeptides of the invention can be fused to another polypeptide or tag, such as a leader or secretory sequence or a sequence which is employed for purification or for detection. In a particular embodiment, the polypeptide of the invention comprises the glutathione-S-transferase protein tag which provides the basis for rapid high-affinity purification of the polypeptide of the invention. Indeed, this GST-fusion protein can then be purified from cells via its high affinity for glutathione. Agarose beads can be coupled to glutathione, and such glutathione-agarose beads bind GST-proteins. Thus, in a particular embodiment of the invention, the polypeptide of the invention is bound to a solid support. In a preferred embodiment, if the polypeptide of the invention comprises a GST moiety, the polypeptide is coupled to a glutathione-modified support. In a particular case, said glutathione modified support is a glutathione-agarose bead. Additionally, a sequence encoding a protease cleavage site can be included between said affinity tag and the polypeptide sequence, thus permitting the removal of the binding tag after incubation with this specific enzyme and thus facilitating the purification of the corresponding protein of interest.

In a particular embodiment, the polypeptide of the invention comprises eight SUMO interacting motif attached through its N-terminus to a GST moiety and through its C-terminus to a detection tag, in particular, the Sv5 tag and comprises, additionally, a protease cleavage site between the GST moiety and the first SUMOylated domain and a polyhistidine tag between the protease cleavage site and the first SUMO interacting motif A schematic representation of such a construct can be seen in FIG. 5. In preferred embodiments, the fusion polypeptide comprises four SUMO interacting motif, preferably SIM2 motifs derived from RNF4 and four SUMO interacting motif, preferably SIM3 motifs derived from RNF4 (FIG. 5), that are arranged, alternatively SIM2-linker-SIM3-linker-SIM2-linker-SIM3-linker-SIM2-linker-SIM3-linker-SIM2-linker-SIM3, wherein the linkers are either natural or artificial linkers.

As mentioned above, the inventors have shown that the polypeptides of the invention can bind SUMOylated proteins. Thus, in another aspect, the invention refers to the use of the polypeptides of the invention for the isolation of SUMOylated proteins. In a particular embodiment, the isolation of said SUMOylated proteins is carried out in vitro and/or ex vivo, for example, as described in the Example 1 accompanying the present invention.

In another aspect, the invention refers to the use of the polypeptide of the invention for the identification of the SUMO substrates. In a particular embodiment, the identification of the SUMO substrates are selected from the group of proteins consisting of tumor suppressor p53 and NF-κB inhibitor IκBα.

In another aspect, the invention refers to a nucleotide sequence encoding the polypeptide of the invention. In a particular embodiment, said sequence is selected from the group comprising SEQ ID NO: 6 and/or SEQ ID NO: 8.

The nucleotide sequences of the invention can alternatively have sequence variations with respect to the original nucleotide sequences (SEQ ID NO: 6 and SEQ ID NO: 8), for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences of the invention and encodes a polypeptide of the invention.

In the sense used in this description, a nucleotide sequence is "substantially homologous" to any of the nucleotide sequences describe above when its nucleotide sequence has a degree of identity with respect to the nucleotide sequence of the invention of at least 60%, advantageously of at least 70%, preferably of at least 85%, and more preferably of at least 95%. A nucleotide sequence that is substantially homologous to the nucleotide sequence of the invention can typically be isolated from a producer organism of the polypeptide of the invention based on the information contained in said nucleotide sequence, or it is constructed based on the DNA sequence shown in SEQ ID NO: 6 and SEQ ID NO: 8, by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art. The identity between two nucleotide sequences is preferably determined by using the BLASTN algorithm (BLAST-Manual, Altschul, S., et al., NCBI NLM NIH Bethesda, Md. 20894, Altschul, S., et al., 1990).

In another aspect, the invention relates to a gene construct, hereinafter gene construct of the invention, comprising said nucleotide sequences of the invention. In a particular embodiment, said gene construct is operatively bound to transcription, and optionally translation, control elements.

The gene construct of the invention can incorporate an operatively bound regulatory sequence of the expression of the nucleotide sequence of the invention, thus forming an expression cassette. As used in this description, the expression "operatively bound" means that the polypeptide of the invention, encoded by the nucleotide sequence of the invention, is expressed in the correct reading frame under the control of expression control, or regulatory sequences.

Control sequences are sequences controlling and regulating the transcription and where appropriate, the translation of the polypeptide of the invention, and include promoter sequences, transcriptional regulator-encoding sequences, ribosome-binding sequences (RBS) and/or transcription termination sequences. In a particular embodiment, said expression control sequence is functional in prokaryotic organisms and cells, for example, bacteria, etc., whereas in another particular embodiment, said expression control sequence is functional in eukaryotic organisms and cells, for example, insect cells, plant cells, mammal cells, etc. Examples of well known promoters suitable for carrying out the invention include constitutive promoters such as those found in some eukaryotic viruses (polyoma virus, adenovirus, SV40, CMV, avian sarcoma virus, hepatitis B virus, metalothionein gen promoter, herpes simplex virus thymidine kinase promoter, retroviral LTR regions, immunoglobulin promoter, actin promoter, EF-1 alpha promoter as well as inducible promoters wherein expression of the downstream gene requires addition of a substance of an exogenous signal to the culture such as the tetracycline promoter, NFKappaB/UV light, Cre/lox, heat shock promoters, regulable RNA polymerase II promoters described in WO/2006/135436 as well as tissue-specific promoters, such as the PSA promoter described in WO2006012221. Advantageously, the construct of the invention further comprises a marker or gene encoding a motif or a phenotype which allows screening the host cell transformed with said construct. In a particular embodiment, the expression of said gene construct is externally controlled. In a more particular embodiment, the expression is externally controlled using the doxycycline Tet-On system.

The gene construct of the invention can be obtained by means of using techniques that are widely known in the state of the art (Sambrook et al., 1989).

The gene construct of the invention can be inserted in a suitable vector. Therefore, in another aspect, the invention relates to a vector, hereinafter vector of the invention, comprising the nucleotide sequence of the invention or the gene construct of the invention. The choice of the vector will depend on the host cell in which it is to be subsequently introduced. In a particular embodiment, the vector of the invention is an expression vector. Suitable vectors for the insertion of the nucleotide sequence of the invention or the gene construct of the invention are vectors derived from prokaryotic expression vectors such as pUC18, pUC19, pGEX-6P-1, Bluescript and their derivatives, mp 18, mp 19, pBR322, pMB9, CoIE1, PCR1, RP4, phage and "shuttle" vectors such as pSA3 and pAT28, yeast expression vectors such as yeast 2 micron plasmid, integration plasmid, yeast episomal plasmid (YEp) vectors, similar and centromeric plasmids, expression vectors in insect cells such as vectors the pAC series and the pVL series, plant expression vectors such as vectors series pIBI, pEarleyGate, pAVA, pCAMBIA, pGSA, pGWB, pMDC, pMY, pORE and similar and expression vectors in eukaryotic cells rather than based on viral vectors (adenovirus, adenovirus associated viruses and retroviruses, and particularly, lentivirus) and non-viral vectors such as pSilencer 4.1-CMV (Ambion), pcDNA3, pcDNA3.1/hyg pHCMV/Zeo, pCR3.1, pEF1/His, pIND/GS, pRc/HCMV2, pSV40/Zeo2, PTRACE-HCMV, pUB6N5-His, pVAX1, pZeoSV2, pCI, pSVL and pKSV-10, pBPV-1, pML2d and pTDT1. By way of illustration, the vector in which said nucleic acid sequence is introduced can be a plasmid which is or is not integrated in the genome of a host cell when it is introduced in said cell. Illustrative, non-limiting examples of vectors in which the nucleotide sequence of the invention or the gene construct of the invention can be inserted include a Tet-On inducible vector for expression in eukaryote cells.

The vector of the invention can be obtained by conventional methods known by persons skilled in the art (Sambrook et al., 1989). In a particular embodiment, said vector is a vector useful for transforming animal cells.

The vector of the invention can be used to transform, transfect, or infect cells which can be transformed, transfected, or infected by said vector. In this sense, the present invention also relates a cell comprising and/or expressing the nucleotide sequences of the invention or a gene construct of the invention, or a vector of the invention. Said cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or HeLa cells or prokaryotic cells such as bacteria, *Escherichia coli* or *Bacillus subtilis*, for example.

Therefore, in another aspect, the invention relates to a non-human animal, hereinafter non-human animal of the invention, comprising and expressing a nucleotide sequence of the invention, or a gene construct of the invention, or a vector of the invention, or a cell of the invention. In a particular embodiment of the invention, the non-human animal of the invention is a mammal, preferably a rodent, more preferably a mouse or a rat.

In another aspect, the invention refers to a process for obtaining a polypeptide of the invention, which comprises culturing a cell of the invention under conditions which allow producing said polypeptide and, if desired, recovering said polypeptide from the culture medium. Conditions for optimizing the culture of said cell will depend on the cell used and are well known to the skilled person in the art. The process for producing the polypeptide of the invention optionally includes isolating and purifying said polypeptide of the invention. The polypeptide of the invention can be purified from the culture medium or from cell extracts (see Example 1). The polypeptide of the invention is conveniently captured using a suitable purification matrix, being, once eluted, concentrated using a commercially available protein concentrating filter, for example, Amicon or Millipore Pellicon, as known in the state of the art.

In another aspect, the invention refers to an in vitro method for the isolation of SUMOylated protein from a sample which comprises
  i) incubating a polypeptide of the invention with said sample in conditions allowing said polypeptide to interact with at least one SUMOylated protein present in said sample; and
  ii) recovering any SUMOylated protein which is bound to said polypeptide.

In a particular embodiment, the recovering step is carried out by means of using an affinity column.

In a particular embodiment, said sample is a cell extract. As explained in the Example 1 accompanying the present invention, in order to purify the SUMOylated protein from cell extracts, cells are first pre-treated with a proteasome inhibitor. The reason for this is that many ubiquitylated and SUMOylated proteins are rapidly turned over by proteasomes, making this transient event difficult to detect. Thus in a preferred embodiment of the invention, when said sample is a cell extract, cells are first pretreated with a proteasome inhibitor previous to obtain said cell extract. In a particular case, such proteasome inhibitor is MG132 or lactacystin.

An additional factor to consider is the presence of deubiquitylating and desumoylating enzymes (isopeptidases) in the cell extract, which can remove the ubiquitin and SUMO molecules from the protein of interest, thereby preventing detection of the ubiquitylated and SUMOylated species. These problems can be avoided, for example, by preparing the extraction buffer with noxious compounds such as the iodoacetamide (IAA) or N-Ethylmaleimide (NEM), which blocks the critical cysteine residue present in the active site of most enzymes of this type. Another important aspect to consider is the conditions under which a protein is ubiquitylated, SUMOylated and degraded, being critical to establish the conditions that promote substrate degradation if ubiquitylated and SUMOylated forms are to be detected. Another factor to consider is the abundance of the protein of interest. In some cases, the modification by ubiquitin and SUMO of an endogenous protein can be assessed, whereas in others, over expression of the target protein is required. Additionally, it is necessary to denature the extract before purification of the target protein to demonstrate that the protein of interest is itself ubiquitylated/SUMOylated and not merely binding to additional co-purified proteins that are ubiquitylated/SUMOylated.

After recovering said SUMOylated protein bound to said polypeptide, elution of said protein of interest can be carried out by means of, for example, incubation with a specific enzyme, such as a protease, when the polypeptide of the invention comprises a target site for such enzymes, facilitating the purification of the corresponding protein, or by deubiquitinating/desumoylation the recovered protein using a deubiquitylation/desumoylation enzymes as described, for example, in WO0406514, or alternatively, using denaturing conditions or by centrifugation methods.

In another aspect, the invention refers to a kit, hereinafter kit of the invention, comprising the polypeptide of the invention. In the present invention, a "kit" is understood as a product containing the different reagents for the carrying out the methods according to the present invention. The kits of the invention may comprise a packing which allows maintaining the reagents within determined limits. Suitable materials for preparing such packings include glass, plastic (polyethylene, polypropylene, polycarbonate and the like), bottles, vials, paper, sachets and the like. The kit of the invention can additionally contain instructions for using the reagents in the method of the invention. Said instructions can be found in the form of printed material or in the form of an electronic support which can store instructions such that they can be read by a subject, such as electronic storage media (magnetic disks, tapes and the like), optical media (CD-ROM, DVD) and the like. The media can additionally or alternatively contain Internet websites providing said instructions. In a particular embodiment, said kit further comprises a solid support. In a more particular embodiment, said support is agarose. In another particular embodiment, the kit of the invention further comprising all the elements necessary to carry out the method disclosed in the present invention.

The following examples illustrate the invention and should not be considered in a limiting sense, but rather in an illustrative sense of the invention Example 1

Methods

Molecular Cloning of Synthetic Oligonucleotides Encoding SIM2 and SIM3 of RNF4.

Synthetic oligonucleotides encoding SIM2 and SIM3 of RNF4 protein (GenBank ID: 6047) were cloned into the PGEX-6P1 vector (Amersham) using specific primers as follows: for TSIM1 (SUBE1) primers with SEQ ID NO: 1 and SEQ ID NO: 2 and for TSIM2 (SUBE2) primer with SEQ ID NO: 3 and SEQ ID NO: 4 were used. This vector was modified introducing a linker, in frame, with a His6 tag and a SV5 epitope upstream and downstream of the multicloning site, respectively, leading to PGEX-6P1 modified vector (SEQ ID NO:5). Such modifications allow the recognition of the protein by specific antibodies. The fragments encoding the SIM2 (SEQ ID NO: 10) and SIM3 (SEQ ID NO: 12) of RNF4 protein were introduced in these constructs, separated by either the natural sequences of RNF4 (TSIM1 or SUBE1) or a polyglycine linker (TSIM2 or SUBE2) (FIG. 4).

Protein Pulldown.

In order to use TSIMs as affinity columns to pulldown SUMOylated proteins, HeLa cells were grown on DMEM medium (Gibco) supplemented with 10% FBS and 1% of antibiotics at 37° C. Thirty minutes before harvest, cells were treated with 20 μM of MG-132 at 37° C. and stressed for 60 minutes by heat shock at 43° C. to induce SUMOylated conjugates. Then cell lysis was performed either in 50 mM sodium fluoride, 5 mM tetra-sodium pyrophosphate, 10 mM beta-glyceropyrophosphate, 1% Igepal CA-630, 2 mM EDTA, 20 mM $Na_2HPO_{4/20}$ mM NaH2PO4 pH 7.5, or 25 mM sodium fluoride, 2.5 mM tetra-sodium pyrophosphate, 5 mM beta-glyceropyrophosphate, 1% Igepal CA-630, 1 mM EDTA, 10 mM Na2HPO4/10 mM NaH2PO4 pH 7.5, 25 mM Tris pH 8.5; 75 mM NaCl, 2.5 mM EDTA, supplemented with 1 mM PMSF and 1.2 mg/ml complete protease inhibitor cocktail (Roche).

Figure 7:
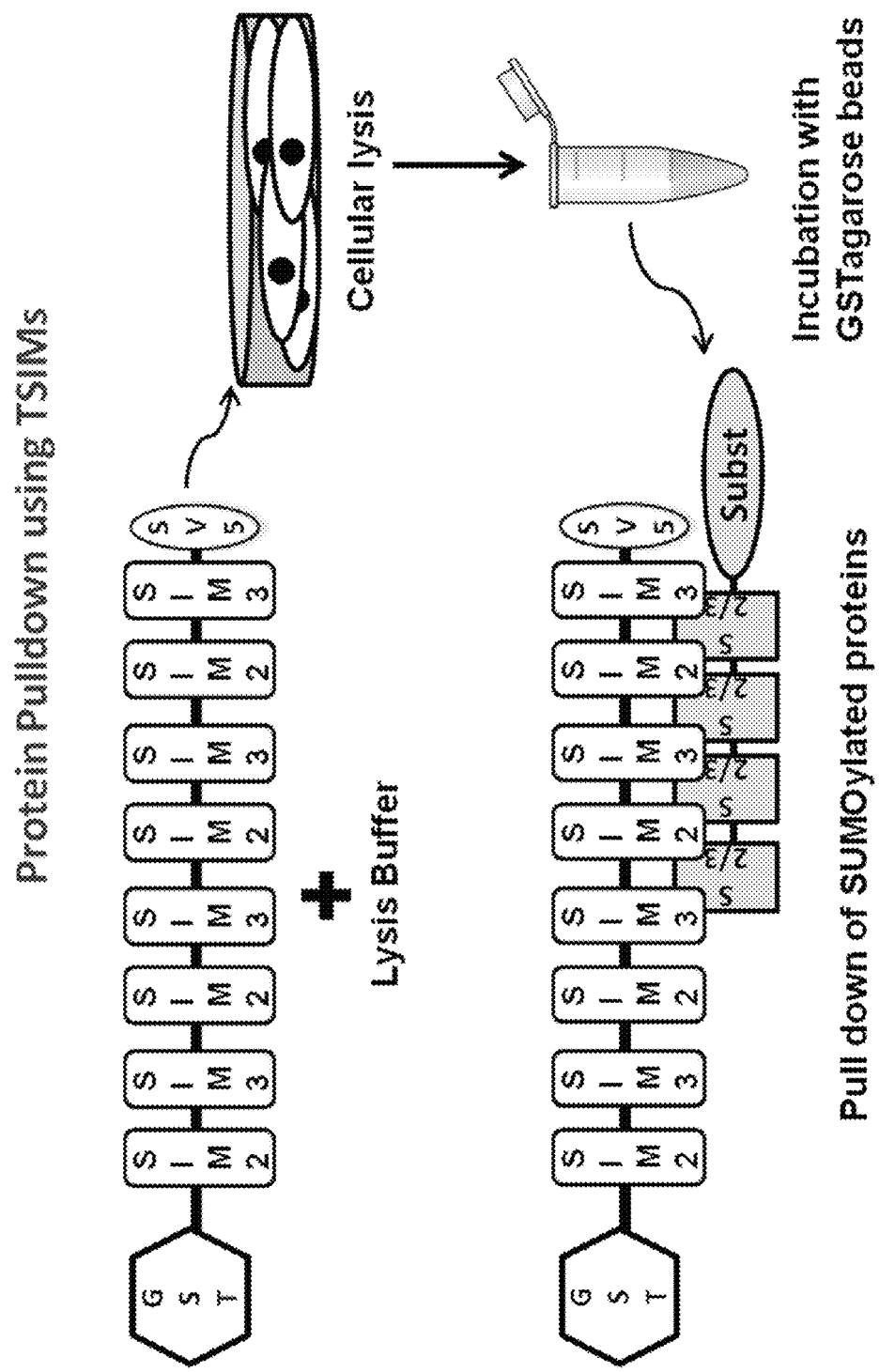
FIG. 7: Schematic representation of protein Pulldown using TSIMs. After cell lysis, TSIMs are able to capture SUMOylated proteins by the affinity that exists between the SIMs domains that constitute TSIMs

Two hundred micrograms of TSIM1 (SUBE1), TSIM2 (SUBE2) or GST (as control) were included or not in the lysis buffer prior sonication, as indicated in the figure legends. Binding step was performed using GST beads (Biontex) with posterior washes with 50 mM Tris pH 8.5; 50 mM NaCl, 5 mM EDTA and 1% Igepal and elution was performed with Lammeli Buffer (FIG. 7).

For the capture of SUMOylated PML, 3 million of breast cancer MCF-7 cells line were stimulated by UV (25 J/m$^2$) and incubated at 37° C. during 4 hours. Cells were resuspended in 1 mL Lysis Buffer containing 50 μM of PR619 (protease inhibitor) and a cocktail of protease inhibitors (Roche). Cells were then sonicated twice for 15 seconds. Lysed cells were then centrifuged during 10 min at 13000 rpm, 4° C. An aliquot of supernatant was kept (Input) and the rest mixed with 200 μg GST control (GST), TSIM1 (SUBE1), TSIM2 (SUBE2) or no TSIMs (SUBEs) and no stimulation (NS), together with GST beads rotating 4 h at 4° C. GST beads were then washed three times with 1 ml of wash buffer (lysis buffer containing only 50 mM NaCl) and GST beads were resuspended in Lamely buffer. For western blot analysis, Input, and beads samples were separated in a 10% polyacrylamide gel and proteins were transferred in a PVDF membrane at 400 mA during 2 hours. Membrane was incubated with anti-PML antibody (Bethyl Laboratories Inc, Texas, USA).

In Vitro SUMO-Chain Assay.

For this assay, it was used a buffer containing an ATP regenerating system, 50 mM Tris pH 7.5, 10 mM MgCl2, 2 mM ATP, 10 mM creatine phosphate (Sigma), 3.5 U/ml of creatine kinase (Sigma), and 0.6 U/ml of inorganic pyrophosphatase (Sigma). Reactions were done as referred: 10 μg of SUMO-1, 2 or 3 or 5 μg (if used in combination with SUMO-2 and SUMO-3), 0.325 μg of Ubc9 (SUMO E2 ligase) and 0.08 μg of purified SAE1/2 (Sumo E1 ligase) (Biomol). Reactions were incubated at 30° C. for 2 hours and stopped by addition of SDS sample buffer. Pulldown assays were done as saving ¹⁄₁₀ of the Input and bind the rest of the reaction with 100 μl of GST-agarose beads and 50 μg of TSIM1 (SUBE1) for 4 h and or overnight at 4° C. rotating, with 1 mM of DTT (Dithiothreitol). After binding, samples were centrifuged at 1200 rpm, 5 min at 4° C. A small fraction was bound to analyse the unbound fraction, and then beads were washed 5 times with 2 ml of PBS 1× with 0.05% of Tween 20. Samples were then eluted in 100 μl (500 BBX3+ 50 μl of PBS/0.05% of Tween20). Reaction products were resolved by SDS-PAGE (10%).

Results

TSIMs Expression and Purification.

TSIMs proteins were expressed on BL-21 *Escherichia coli* strain, according to standard procedures. After that, bacteria pellet was harvested by centrifugation and cell lysis were performed in PBS/0.5M NaCl by sonication. The same concentration of salt was maintained along the procedure including storage conditions. The resulted debris was separated also by centrifugation and the resulted supernatant was incubated with GST (Glutathione S-transferase) agarose beads. The TSIMs were then obtained by elution using reduced glutathione. Recombinant proteins were maintained in PBS/0.5M NaCl and 10% of glycerol, at −80° C. until use.

TSIM1 (SUBE1) Interacts with PolySUMO Chains.

Figure 8:
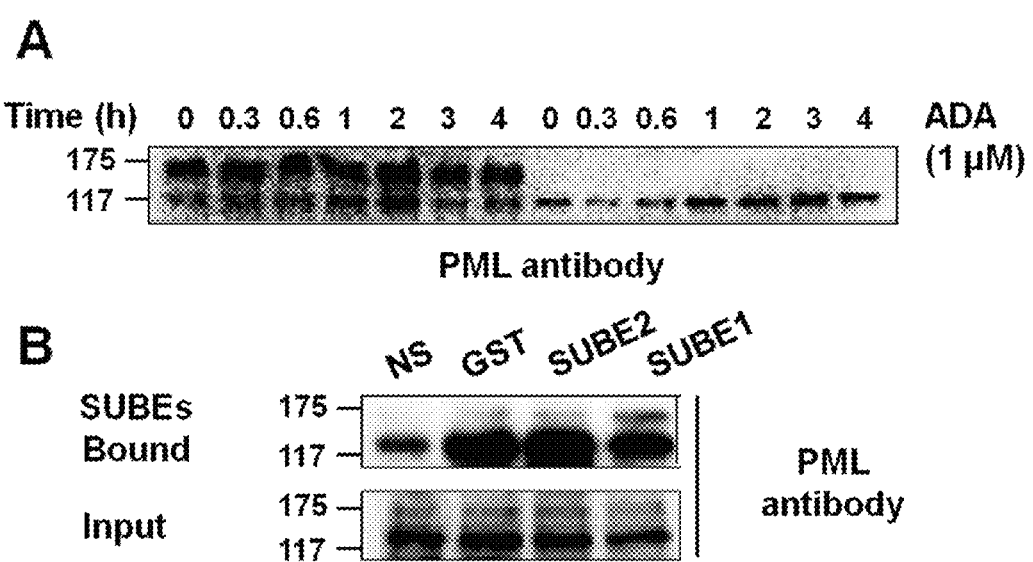
FIG. 8: Capture of SUMOylated PML and SUMO chains using TSIMs. (A) SUMOylated PML can be purified from MCF7 cell extracts before and after treatment with 1 uM of Adriamycin (ADA), using TSIM1 (SUBE1) but not TSIM2 (SUBE2). (B) The association of TSIM1 (SUBE1) with PML is stronger than the one observed with the TSIM2 (SUBE2) or GST control. (C) PolySUMO chains can be purified by TSIM1 (SUBE1) from an in vitro SUMOylation reaction using only SUMO1, SUMO2, SUMO3 or a mix SUMO2/SUMO3. GST was used as negative control. Numbers to the left of the photographs indicate the molecular weight marker. FT: flow through, fraction not retained in the purification column (pull-down).
Figure 8:
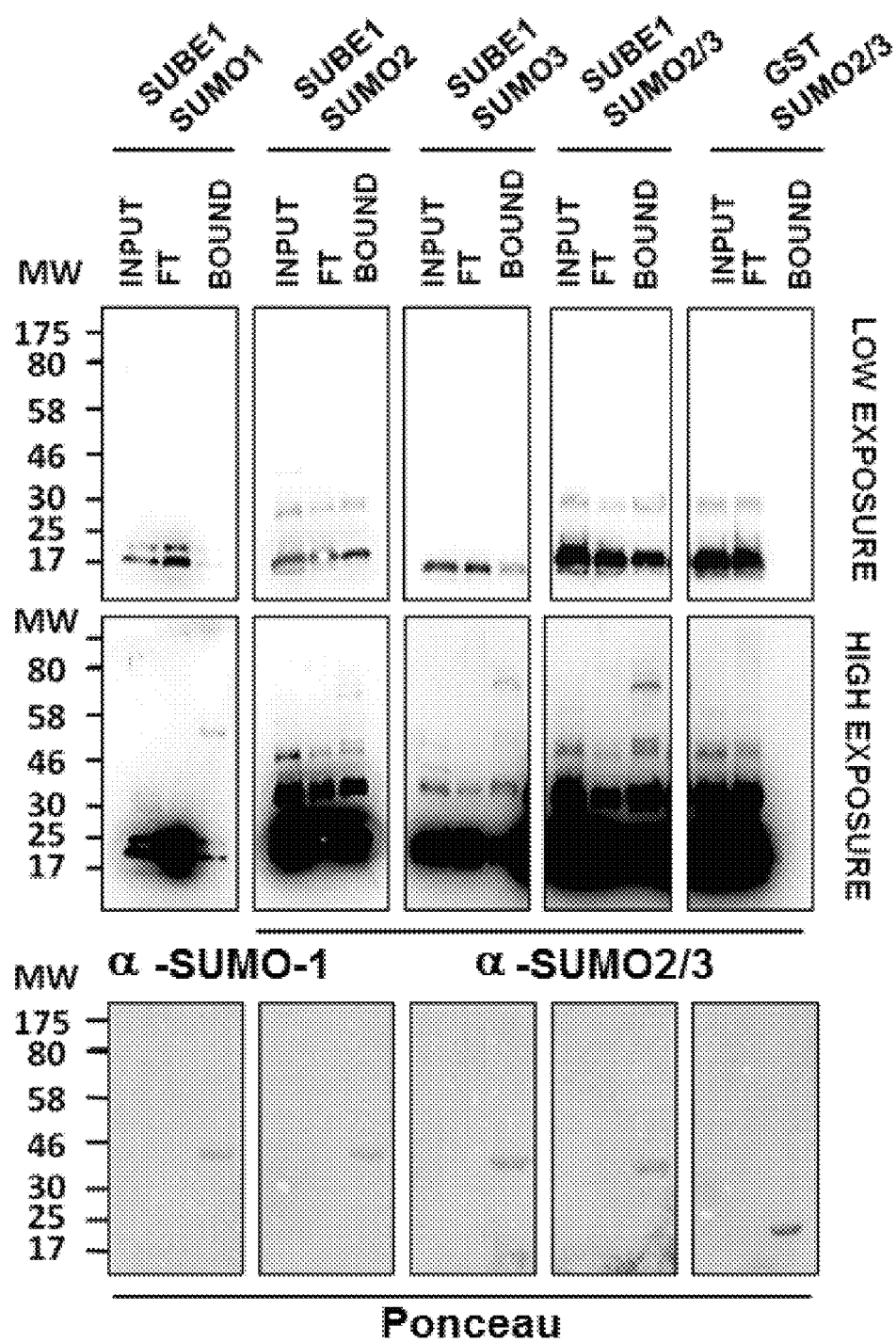

To verify the functionality of these recombinants TSIM-interacting constructs, it was analyzed their capacity to interact with the natural substrate of RNF4, SUMOylated PML. It was found that the engineered TSIM1 (SUBE1) but not the TSIM2 (SUBE2) interact with SUMOylated PML purified from MCF7 cells (breast cancer cell line) stimulated or not with a genotoxic insult with 1 μM of Adriamycin (ADA) (FIG. 8A). Under the used conditions SUMOylated PML show little or not interaction with TSIM2 (SUBE2) or GST control (FIG. 8B). However the unmodified form of PML interacts with these proteins and with the non-specific (NS) control made only with agarose beads (FIG. 8B). As the SIMs of RNF4 interacts with PML only when it is polySUMOylated, the capacity of TSIM1 (SUBE1) to interact with polySUMO chains was tested using an in vitro SUMOylation assay. In this system no substrate and no SUMO E3 enzyme was added, resulting in the modest production of polySUMO chains. Chains containing up to 2 molecules of SUMO-1 or 3 molecules of SUMO-2 or SUMO-3 can only be seen in the input (FIG. 8C high exposure). However, chains containing more than 4 SUMO chains can be recovered in the TSIM1-bound fraction, been the most efficient, the pull-down made with a mix of SUMO-2 and SUMO3 (FIG. 8C high exposure). Under these conditions TSIM1 (SUBE1) does not bind to free SUMO-1 but show a modest binding to free SUMO-3 and more importantly to free SUMO-2 and SUMO-3 suggesting the natural preferences of the SIM2 and SIM3 of RNF4 (FIG. 8C low exposure). Furthermore, no GST-binding of free or polySUMO chains were observed. Altogether these results indicate that TSIM1 (SUBE1) binds to polySUMOylated proteins such as PML or to SUMO-chains containing more than 4 SUMO moieties.

TSIMs Show Higher Affinity for polySUMO Chains.

Figure 9:
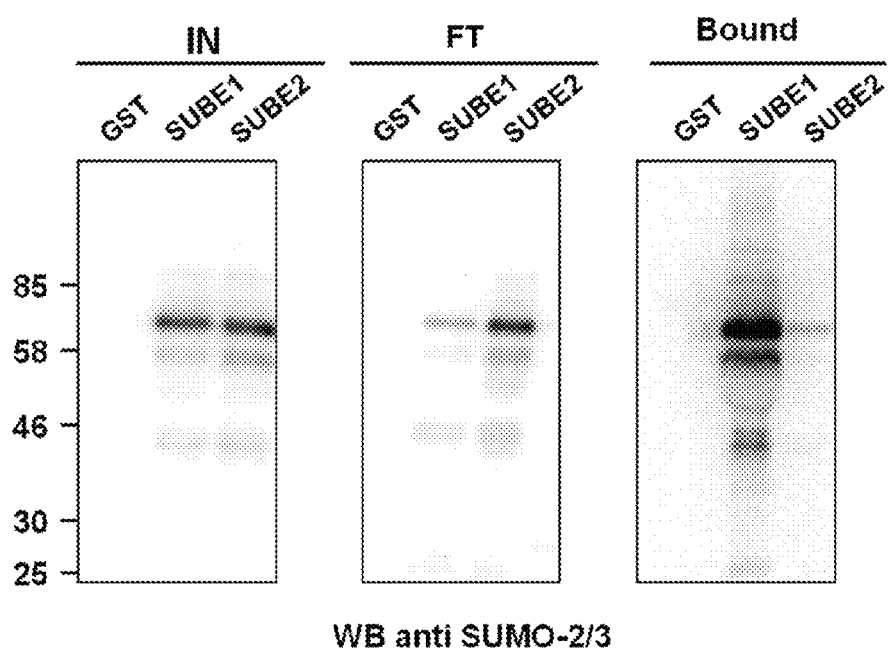
FIG. 9: Analysis of artificial SUMO chains using TSIMs. (A) The capacity of TSIMs to interact with a SUMO-2 fusion containing 4 moieties was evaluated by a GST pulldown. GST was used as negative control. Numbers to the left of the photographs indicate the molecular weight marker. (B) The affinity of both TSIMs for the SUMO-fusion was estimated by surface plasmon resonance (SPR). Estimated affinities for TSIM1 (SUBE1) and TSIM2 (SUBE2) was of 42.5 μM and >300 μM respectively. IN: input; FT: flow through, fraction not retained in the purification column (pull-down).

To investigate the affinity that TSIMs have towards polySUMOylated chains, the inventors have used a SUMO-fusion containing 4 molecules (Taham M H et al, 2008). Two distinct approaches, GST pull-down and Surface Plasmon Resonance (SPR), show that TSIM1 (SUBE1) has higher affinity for this recombinant tetrameric SUMO fusion. A GST-pull down shows significant differences in affinity between TSIM1 (SUBE1) or TSIM2 (SUBE2) and the SUMO-fusion (FIG. 9A). Using SPR, those affinities were estimated to 43.6 □M and >400 □M for TSIM1 (SUBE1) and TSIM2 (SUBE2) respectively (FIG. 9B). SPR experiments were performed on a Biacore 3000 system, equilibrated at 25° C. in HBS-EP buffer (0.01 M HEPES pH 7.4, 0.15 M NaCl, 3 mM EDTA, 0.005% surfactant P20) (Biacore), using a CM5 sensor chip with a density of approximately 9000 resonance units (RU pg/mm$^2$) covalently immobilized anti-GST antibody (Biacore). Tandem GST-fused SIM domains were captured on the sensor chip at medium (200-250 RU) densities. Mono-ubiquitin (Sigma Aldrich) or the ubiquitin-like molecules SUMO-1, -2, and SUMO-3 (produced as previously described (Rodriguez et al, 1999)) were then injected for 30 s at a flow rate of 30 μl/min, and tetra-SUMO2 (Bruderer et al., 2011) for 50 s at 30 μl/min. All injections were done randomly.

The data obtained by SPR confirmed that TSIM1 (SUBE1) recognize polySUMO-chains whereas TSIM2 (SUBE2) doesn't. Furthermore the results show in the present invention underline the importance of the acidic aminoacids of the SIMs and the linker region between SIMs in the recognition process.

Purification of Total polySUMOylated Proteins Induced after Cellular Stress.

Figure 10:
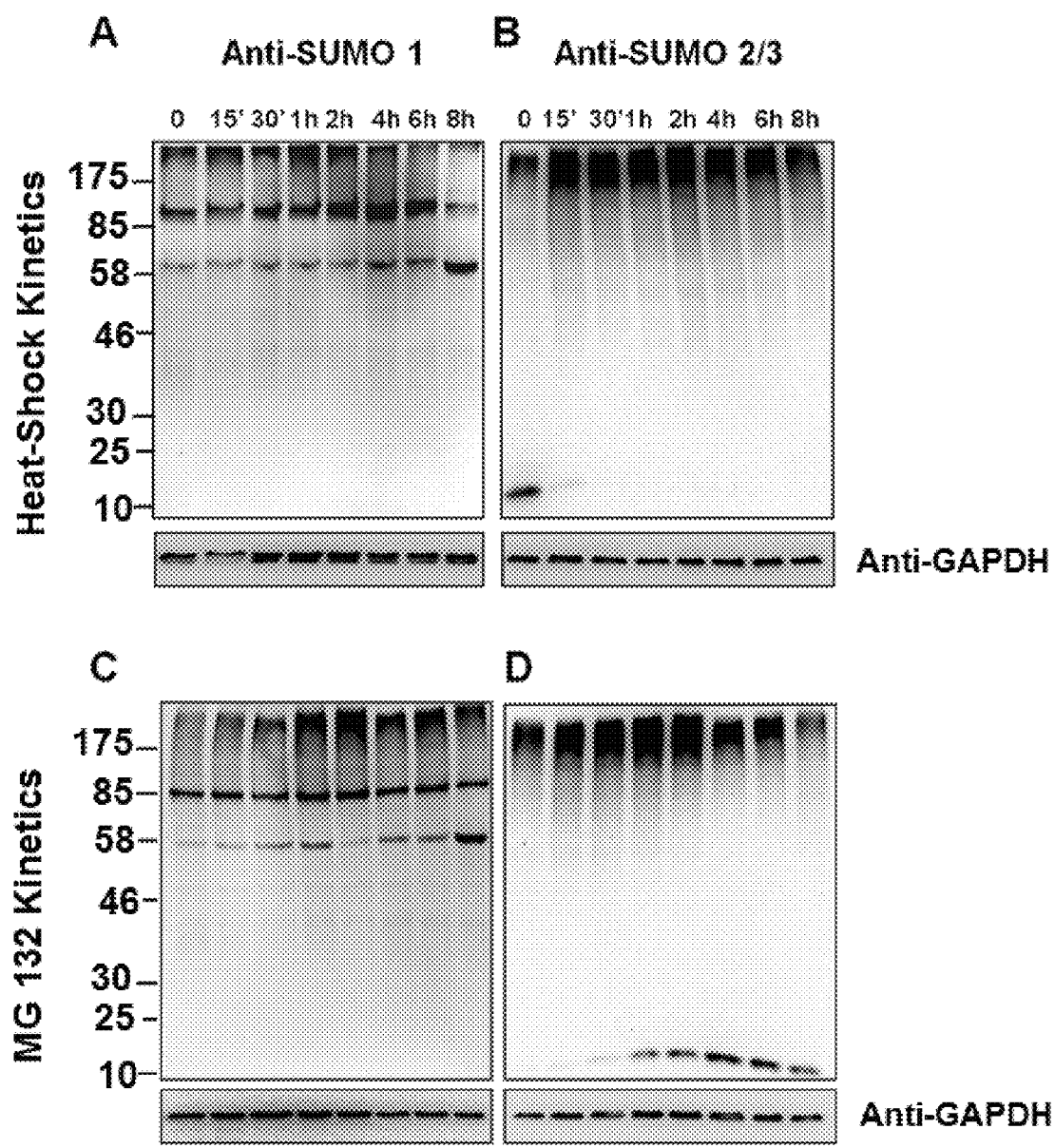
FIG. 10: Accumulation of SUMOylated proteins after heat shock at 43° C. and inhibition of the proteasome with MG-132 treatment. HeLa cells were stressed at 43° C. (A, B) or treated with 20 μM of proteasome inhibitor MG132 (C, D) during the indicated times. After cell lysis, total cell extracts were analyzed by Western blot with anti SUMO-1 (A, C) or anti SUMO-2/3 (B, D) antibodies. Numbers to the left of the photographs indicate the molecular weight marker. Anti-GAPDH was used as load control.

To investigate if TSIMs can interact with total SUMOylated proteins purified cell extracts were used set up conditions to accumulate SUMOlylated proteins using heat shock stress treatment (43° C.) on HeLa cells (FIGS. 10A and B).

Western blot analysis carried out on these HeLa cells shows that SUMOylated proteins are increased after 15 to 30 minutes of heat shock with a prominent accumulation after 60 minutes (FIGS. 10A and B). It was also observed that while SUMO-2/SUMO-3 was accumulated 15 minutes after these treatments, the accumulation of SUMO-1 was more obvious after 60 minutes of treatment. Interestingly both SUMO-1 and SUMO-2/SUMO-3 are accumulated with similar timing suggesting a simultaneous activation of the conjugation of both types of modifiers (FIGS. 10A and B).

Recently, SUMOylation has been associated to ubiquitylation and it is known that inhibition of the proteasome activity accumulates SUMOyated proteins. To evaluate the role of the proteasome in the metabolism of proteins conjugated with SUMO and to explore further accumulation conditions of SUMOylated proteins, kinetics of proteasome inhibitors were performed in HeLa cells (FIGS. 10C and D). Cells were treated with 20 µM of proteasome inhibitor MG132 for the indicated times. It can be easily observed that SUMOylated proteins are increased after 30 minutes of MG132 treatment. For this reason, we are selected the above mentioned conditions, 30 minutes of MG132 treatment and 60 minutes of heat shock, to accumulate/preserve SUMOylated proteins.

TSIMs as Affinity Columns

Figure 11:
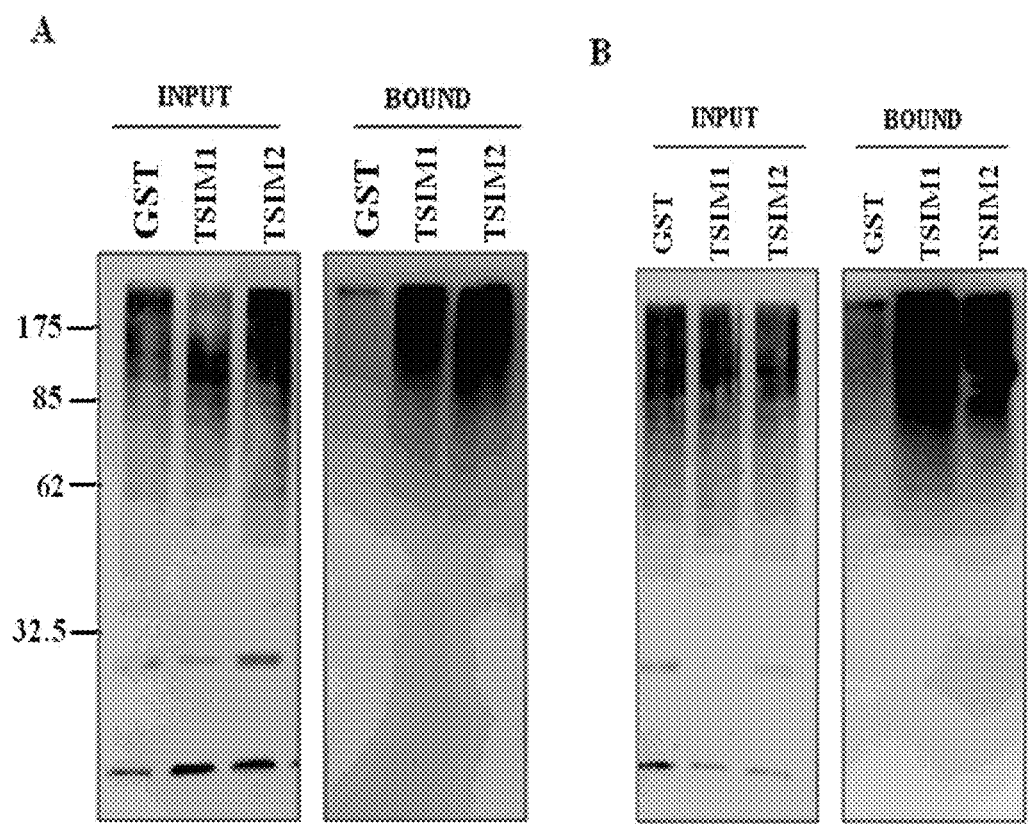
FIG. 11: Capture and analysis of SUMOylated proteins from cell extracts. TSIMs were capable to pulldown SUMOylated proteins from Hela extracts, after 30 minutes of 20 μM of MG-132 treatment, followed by 60 minutes of heat shock (43° C.) to increase the level of SUMOylated conjugates. Two extraction/binding buffer conditions were used. A) Buffer containing phosphatase inhibitors but no NaCl. B) Buffer containing 75 mM NaCl. IN-Input. Bound-Captured fractions. GST as negative control. Numbers to the left of the photographs indicate the molecular weight marker.

In order to verify the use of TSIMs as affinity columns to capture SUMOylated proteins, the invention used GST pulldowns to capture SUMOylated proteins from HeLa cells extracts. To enrich SUMOylated proteins in cells, various stimuli have been reported. Here, in present invention, a pre-treatment during 30 minutes with proteasome inhibitors followed by heat shock stimulation at 43° C. during 60 minutes was used. Several extraction conditions were tested to increase an efficient extraction and optimal capture of SUMOylated proteins. Due to the architecture and properties of each of the TSIMs, both SUMO traps show optimal capture conditions in different buffers. The absence of NaCl in the buffer favours TSIM1 (SUBE1) for the capture of SUMOylated proteins (FIG. 11A). In contrast the capture efficiency of TSIM2 (SUBE2) is improved in the presence of 75 mM NaCl (FIG. 11B), in conditions where the input was comparable for both extraction/binding conditions.

Figure 12:
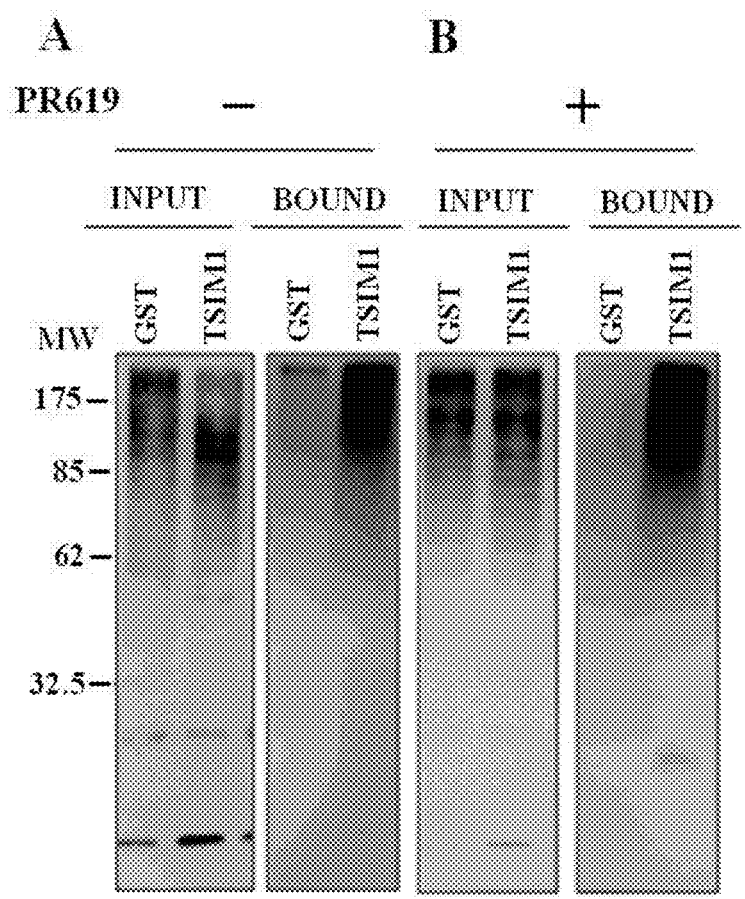
FIG. 12: The inhibition of SUMO-hydrolases favors the TSIM-mediated capture of SUMOylated proteins. HeLa cells treated with 20 μM of MG-132, followed by 60 minutes of heat-shock (43° C.). Ten minutes before lysis, cells were treated (+) or not (−) with protease inhibitor PR619 at 100 μM. TSIM-bound fractions were blotted against anti-SUMO 2/3 antibody. Numbers to the left of the photographs indicate the molecular weight marker.

Interestingly the capacity of TSIM1 (SUBE1) to capture SUMOylated targets can be increased after addition of PR619 (Life-Sensors), the first cell permeable inhibitor of de-ubiquitylating/de-SUMOylatin enzymes (FIG. 12).

BIBLIOGRAPHY

Altschul S F, Gish W, Miller W, Myers E W, Lipman D J. 1990. Basic local alignment search tool. J Mol Biol. 215(3):403-10.

Bernier-Villamor V., Sampson D. A., Matunis M. J. & Lima C. D. 2002. Structural basis for E2-mediated SUMO conjugation revealed by a complex between ubiquitin conjugating enzyme Ubc9 and RanGAP1. Cell 108, 345-356.

Bruderer R, Tatham M H, Plechanovova A, Matic I, Garg A K, Hay R T. 2011. Purification and identification of endogenous polySUMO conjugates. EMBO Rep. February; 12(2):142-8.

Geiss-Friedlander R. and Melchior F. 2007. Concepts in SUMOylation: a decade on Nature reviews molecular cell biology 8; 947-956.

Golebiowski F., Matic I., Tatham M., H., Cole V., Yin Y., Nakamura A., Cox J., Barton G., J., Mann M., and Hay R. T. 2009. System-Wide Changes to SUMO Modifications in Response to Heat Shock. Sci. Signal., 2 (72) 24.

Hecker C. M., Rabiller M., Haglund K., Bayer P. and Dikic I. 2006. Specification of SUMO1- and SUMO2-interacting motifs. J. Biol. Chem. 281, 16117-16127.

Hay R. 2005. SUMO: A History of Modification. Molecular Cell, 18 1-12.

Hayashi T., Seki M., Maeda D., Wang W., Kawabe Y., Seki T. J. 2002. Ubc9 is essential for viability of higher eukaryotic cells. Exp. Cell Res. 280, 212-221.

Johnson E. S. 2004. Protein modification by SUMO. Annu. Rev. Biochem 73:355-382.

Kagey M. H., Melhuish T. A., and Wotton D. 2003. The polycomb protein Pc2 is a SUMO E3. Cell 113, 127-137.

Kahyo T., Nishida T., Yasuda H. 2001. Involvement of PIAS1 in the sumoylation of tumor suppressor p53. *Mol. Cell* 8 (3): 713-8.

Kerscher O., Felberbaum R., Hochstrasser M. 2006. Modification of proteins by ubiquitin and ubiquitin-like proteins. Annu. Rev. Cell Dev. Biol. 22, 159-180.

Lapenta, V., Chiurazzi, P., van der Spek, P., Pizzuti, A., Hanaoka, F. and Brahe, C. 1997. SMT3A, a human homologue of the *S. cerevisiae* SMT3 gene, maps to chromosome 21qter and defines a novel gene family. Genomics 40, 362-366.

Matunis, M. J., Coutavas, E. and Blobel, G. 1996. A novel ubiquitin-like modification modulates the partitioning of the Ran-GTPase-activating protein RanGAP1 between the cytosol and the nuclear pore complex. J. Cell Biol. 135, 1457-1470.

Mahajan, R., Delphin, C., Guan, T., Gerace, L. and Melchior, F. (1997) A small ubiquitin-related polypeptide involved in targeting RanGAP1 to nuclear pore complex protein RanBP2. Cell 88, 97-107.

Miteva M., Keusekotten K., Hofmann K., Praefcke G., and Jürgen Dohmen R. Sumoylation as a Signal for Polyubiquitylation and Proteasomal Degradation. 2010. Chapter 16. Pp 195-214. Bookshelf ID: NBK25447 Conjugation and Deconjugation of Ubiquitin Family Modifiers edited by Marcus Groettrup.

Rodriguez M S, Desterro J M, Lain S, Midgley C A, Lane D P, Hay R T. SUMO-1 modification activates the transcriptional response of p53. 1999. EMBO J. November 15; 18(22):6455-61.

Rodriguez M. S., Dargemont C. and Hay R. T. 2001. SUMO-1 conjugation in vivo requires both a consensus modification motif and nuclear targeting. J. Biol. Chem. 276, 12654-12659.

Sambrook J., MacCallum P. Molecular cloning, a Laboratory Manual. 1989. 2nd ed., Cold Spring Harbor Laboratory Press, N.Y., Vol 1-3

Saitoh H, Hinchey J. 2000. Functional heterogeneity of small ubiquitin-related protein modifiers SUMO-1 versus SUMO-2/3. J Biol Chem; 275:6252-6258.

Sampson D A, Wang M, Matunis M J. 2001. The small ubiquitin-like modifier-1 (SUMO-1) consensus sequence mediates Ubc9 binding and is essential for SUMO-1 modification. J Biol Chem. 276(24):21664-9.

Seufert, W., Futcher, B., and Jentsch, S. 1995. Role of ubiquitin-conjugating enzyme in degradation of S- and M-phase cyclins. Nature 373, 78-81.

Seeler, J., S. and Dejean, A. 2003. Nuclear and unclear functions of SUMO. Nat Rev Mol Cell Biol. 9:690-9.

Schmidt, D. and Muller, S. 2002. Members of the PIAS family act as SUMO ligases for c-Jun and p53 and repress p53 activity. Proc. Natl. Acad. Sci. U.S.A. 99, 2872-2877.

Song, J., Durrin, L. K., Wilkinson, T. A., Krontiris, T. G. & Chen, Y. 2004. Identification of a SUMO-binding motif that recognizes SUMO-modified proteins. Proc. Natl. Acad. Sci. USA 101, 14373-14378.

Tatham M. H., Jaffray E., Vaughan O. A., Desterro J. M., Botting C. H, Naismith J. H., Hay R. T. 2001. Polymeric chains of SUMO-2 and SUMO-3 are conjugated to protein substrates by SAE1/SAE2 and Ubc9. J. Biol. Chem. 276, 35368-35374.

Tatham, M. H., Geoffroy, M. C., Shen, L., Plechanovova, A., Hattersley, N., Jaffray, E. G., Palvimo, J. J., Hay R. T. 2008. RNF4 is a poly-SUMO-specific E3 ubiquitin ligase required for arsenic-induced PML degradation. Nat Cell Biol. 10(5):538-46.

Yeh, E. T. 2009. SUMOylation and De-SUMOylation: wrestling with life's processes. J. Biol. Chem. 284, 8223-8227.

Wilkinson K., A. and Henley. J., M. 2010. Mechanisms, regulation and consequences of protein SUMOylation. Biochem. J. 428, 133-145.

Xu J., He Y., Qiang B., Yuan J., Peng, X. and Pan, X. M. 2008. A novel method for high accuracy sumoylation site prediction from protein sequences. BMC Bioinformatics 9, 8.

The invention claimed is:

1. A polypeptide comprising at least eight SUMO interacting motifs (SIM) arranged in tandem, wherein said SUMO interacting motifs are linked to each other by a natural amino acid sequence linker.

2. The polypeptide according to claim 1, wherein the at least eight SUMO interacting motifs (SIMs) of claim 1 are present in a protein selected from the group consisting of: PML, Daxx, UBA2, PIAS, RNF4 ligase.

3. The polypeptide according to claim 1, wherein the at least eight SUMO interacting motifs (SIMs) of claim 1 are selected from the group consisting of: SIM1, SIM2, SIM3, SIM4, and combinations thereof.

4. The polypeptide according to claim 1, wherein the at least eight SUMO interacting motifs (SIMs) of claim 1 are SIM2 and/or SIM3, from the RNF4 ligase protein.

5. The polypeptide according to claim 1, wherein the polypeptide comprises four SIM2 and four SIM3 motifs.

6. The polypeptide according to claim 1, consisting of the amino acid sequence encoded by the nucleotide sequence SEQ ID NO: 7.

7. The polypeptide according to claim 1, wherein the natural sequence linker is present in RFN4.

8. A process for obtaining a polypeptide according to claim 1, which comprises culturing a cell comprising a nucleotide encoding at least eight SUMO interacting motifs (SIM) arranged in tandem and linked to each other by a natural amino acid sequence linker, under the control of a promoter wherein the polypeptide is expressed, and, recovering said polypeptide from the culture medium.

9. An in vitro and/or ex vivo method for the isolation of a SUMOylated protein from a sample which comprises
 i) incubating the polypeptide of claim 1 with said sample in conditions allowing said polypeptide to interact with at least one SUMOylated protein present in said sample; and
 ii) recovering the SUMOylated protein which is bound to said polypeptide.

10. A kit comprising the polypeptide of claim 1 and instructions for use of said polypeptide.

11. The kit according to claim 10 further comprising a solid support.

12. An in vitro and/or ex vivo method for identifying SUMO substrates from a sample which comprises
 i) incubating the polypeptide of claim 1 with said sample in conditions allowing said polypeptide to interact with at least one substrate of SUMO proteins present in said sample;
 ii) recovering any SUMO substrates which is bound to said polypeptide; and
 iii) identifying SUMO substrates recovered in the previous step.

13. The method according to claim 12 wherein the SUMO substrates are selected from: tumor suppressor p53 and NF-κB inhibitor IκBα.

14. A nucleotide sequence encoding a polypeptide comprising at least eight SUMO interacting motifs (SIM) arranged in tandem, wherein said SUMO interacting motifs are linked to each other by a natural amino acid sequence linker.

15. The nucleotide sequence according to claim 14, wherein said nucleotide sequence is SEQ ID NO: 6.

16. A gene construct comprising the nucleotide sequence of claim 14, operatively linked to transcription control elements.

17. A vector comprising the nucleotide sequence of claim 14.

18. A cell comprising the nucleotide sequence of claim 14.

* * * * *